US008304418B2

(12) United States Patent
Kluge

(10) Patent No.: US 8,304,418 B2
(45) Date of Patent: Nov. 6, 2012

(54) PYRAZOLOPYRIMIDINONE KINASE INHIBITOR

(75) Inventor: Arthur F. Kluge, Lincoln, MA (US)

(73) Assignee: Agennix AG, Heidelberg (DE)

( * ) Notice: Subject to any disclaimer, the term of this patent is extended or adjusted under 35 U.S.C. 154(b) by 204 days.

(21) Appl. No.: 12/602,021

(22) PCT Filed: May 28, 2008

(86) PCT No.: PCT/EP2008/056569
§ 371 (c)(1),
(2), (4) Date: Dec. 1, 2009

(87) PCT Pub. No.: WO2008/145678
PCT Pub. Date: Dec. 4, 2008

(65) Prior Publication Data
US 2010/0160350 A1    Jun. 24, 2010

Related U.S. Application Data

(60) Provisional application No. 60/932,155, filed on May 29, 2007.

(30) Foreign Application Priority Data

Jul. 26, 2007    (EP) .................................... 07113226

(51) Int. Cl.
*A01N 43/90* (2006.01)
*A61K 31/519* (2006.01)
*C07D 487/00* (2006.01)

(52) U.S. Cl. ..................................... 514/262.1; 544/262
(58) Field of Classification Search ......................... None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni et al. | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,710,384 A | 12/1987 | Rotman | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 5,736,137 A | 4/1998 | Anderson et al. | |
| 5,776,456 A | 7/1998 | Anderson et al. | |
| 5,843,437 A | 12/1998 | Hamill et al. | |

FOREIGN PATENT DOCUMENTS

| WO | WO 00/21926 | 4/2000 |
|---|---|---|
| WO | WO 01/87337 | 11/2001 |
| WO | WO 01/97338 | 12/2001 |
| WO | WO 03/033499 | 4/2003 |
| WO | WO 2004/092139 | 10/2004 |
| WO | WO 2005/026129 | 3/2005 |
| WO | WO 2005/063765 | 7/2005 |

OTHER PUBLICATIONS

Wolff et. al., "Burger's Medicinal Chemistry and Drug Discovery," 5th Ed. Part 1, pp. 975-977 (1995).*
Banker, et. al., Modern Pharmaceuticals, (1996), p. 596.*
Alminger et al., Chem. Abstracts, 110: 692 (57664p) (1989).
Bach et al., Roscovitine Targets, Protein Kinases and Pyridoxal Kinase, J. Biol. Chem., 280(35): 31208-31219 (2005).
Baughn et al., A Novel Orally Active Small Molecule Potently Induces G1 Arrest in Primary Myeloma Cells and Prevents Tumor Growth by Specific Inhibition of Cyclin-Dependent Kinase 4/6,Cancer Res., 66(15): 7661-7667 (2006).
Beach et al., p21 is a universal inhibitor of cyclin kinases, Nature, 336: 701-704 (1993).
Bible et al., Cytotoxic synergy between Flavopiridol (NSC 649890, L86-8275) and Various Antineoplastic Agents: The Importance of Sequence of Administration, Cancer Res., 57: 3375-3380 (1997).
Blangy et al., Phosphorylation by p34cdc2 Regulates Spindle Association of Human Eg5, a Kinesin-Related Motor Essential for Bipolar Spindle Formation In Vivo, Cell, 83: 1159-1169 (1995).
Bundgaard et al., Chem. Abstracts, 93: 340 (137935y) (1980).
Bundgaard et al., Chem. Abstracts, 95: 372 (138493f) (1981).
Bundgaard et al., Chem. Abstracts, 95: 381 (138592n) (1981).
Bundgaard et al., Hydrolysis of N-(α-hydroxybenzyl) benzamide and other N-(α-hydroxyalkyl) amide derivatives: implications for the design of N-acyloxyalkyl-type implications for the design of N-acyloxyalkyl-type prodrugs, Int. J. of Pharmaceutics, (Elsevier), 22: 45-46 (1984).
Bundgaard et al., A Novel Solution-Stable, Water-Soluble Prodrug Type for Drugs Containing a Hydroxyl or an NH-Acidic Group, J. Med. Chem., 32(12): 2503-2507 (1989).
Bundgaard et al., Chem. Abstracts, 117: 418 (14347q) (1992).
Burr et al., Chem. Abstracts, 115: 20 (64029s) (1991).
Caligiuri et al., A Proteome-Wide CDK/CRK-Specific Kinase Inhibitor Promotes Tumor Cell Death in the Absence of Cell Cycle Progression, Chem. Biol., 12: 1103-1115 (2005).
Connell-Crowley et al., Cyclin D1/Cdk4 Regulates Retinoblastoma Protein-mediated Cell Cycle Arrest by Site-pecific Phosphorylation, Mol. Biol. Cell, 8: 287-301 (1997).
Cordon-Cardo, C., Mutations of Cell Cycle Regulators. Biological and Clinical Implications for Human Neoplasia, Am. J. Pathol., 147(3): 545-560 (1995).

(Continued)

*Primary Examiner* — Jeffrey Murray
(74) *Attorney, Agent, or Firm* — Leon R. Yankwich; David G. O'Brien; Yankwich & Associates, P.C.

(57) ABSTRACT

The present invention provides a novel pyrazolo[3,4-d]pyrimidin-4-one, specifically a derivative of 1-(pyridine-4-yl)-pyrazolo[3,4-d]pyrimidin-4-one. This compound is a kinase inhibitor that shows unexpected anti-proliferative activity against cells, including against tumor cells, and anti-tumor activity in xenograft tumor models. The compound or a suitable salt or prodrug thereof is useful for the treatment of individuals suffering from a cancer or another proliferative disorder or disease.

10 Claims, 10 Drawing Sheets

OTHER PUBLICATIONS

Davidsen et al., N-(Acyloxyalkyl) pyridinium Salts as Soluble Prodrugs of a Potent Platelet Activating Factor Antagonist, J. Med. Chem., 37(26): 4423-4429 (1994).

DePinto et al., In vitro and in vivo activity of R547: a potent and selective cyclin-dependent kinase inhibitor currently in phase I clinical trials, Mol. Cancer Ther., 5(11): 2644-2658 (2006).

Draetta, Cell cycle control in eukaryotes: molecular mechanisms of cdc2 activation, Trends Biochem. Sci., 15: 378-382 (1990).

Fischer, P.M., The Use of CDK Inhibitors in Oncology: A Pharmaceutical Perspective, Cell Cycle, 3(6): 742-746 (2004).

Fischer et al., Recent progress in the discovery and development of cyclin-dependent kinase inhibitors, Expert Opin. Investig. Drugs, 14(4): 457-477 (2005).

Golan et al., The Cyclin-Ubiquitin Ligase Activity of Cyclosome/APC is Jointly Activated by Protein Kinases Cdk1-Cyclin B and Plk, J. Biol. Chem., 277(18): 15552-15557 (2002).

Huwe et al., Small Molecules as Inhibitors of Cyclin-Dependent Kinases, Angew Chem. Int. Ed. Engl., 42: 2122-2138 (2003).

Jiang et al., Altered expression of the cyclin D1 and retinoblastoma genes in human esophageal cancer, Proc. Natl. Acad. Sci. USA, 90: 9026-9030 (1993).

Joshi et al., In vitro antitumor properties of a novel cyclin-dependent kinase inhibitor, P276-00, Mol. Cancer Ther., 6(3): 918-925(2007).

Kamb et al., A Cell Cycle Regulator Potentially Involved in Genesis of Many Tumor Types, Science, 264: 436-440 (1994).

Kansey et al., Physicochemical High Throughput Screening: Parallel Artificial Membrane Permeation Assay in the Description of Passive Absorption Processes, J. Med. Chem., 41(7): 1007-1010 (1998).

Karp et al., Molecular foundations of cancer: New targets for intervention, Nat. Med., 1(4): 309-320 (1995).

Kim et al., Splicing Factors Associate with Hyperphosphorylated RNA Polymerase II in the Absence of Pre-mRNA, J. Cell Biol., 136(1): 19-28 (1997).

Kitagawa et al., The consensus motif for phosphorylation by cyclin D1-Cdk4 is different from that for phosphorylation by cyclin A/E-Cdk2, EMBO J., 15(24): 7060-7069 (1996).

Lien et al., Therapeutic peptides, Trends in Biotechnology, 21(12): 556-562 (2003).

Listovsky et al., Cdk1 is Essential for Mammalian Cyclosome/APC Regulation, Exp. Cell Res., 255: 184-191 (2000).

Markwalder et al., Synthesis and Biological Evaluation of 1-Aryl-4,5-dihydro-1H-pyrazolo[3,4-d]pyrimidin-4-one Inhibitors of Cyclin-Dependent Kinases, J. Med. Chem., 47: 5894-5911 (2004).

Mateyak et al., c-Myc Regulates Cyclin D-Cdk4 and -Cdk6 Activity but Affects Cell Cycle Progression at Multiple Independent Points, Mol. Cell Biol., 19(7): 4672-4683 (1999).

O'Conner et al., Regulation of apoptosis at cell division by p34cdc2 phosphorylation of surviving, Proc. Natl. Acad. Sci. USA, 97(24): 13103-1317 (2000).

Ongkeko et al., Inactivation of Cdc2 increases the level of apoptosis induced by DNA damage, J. Cell Sci., 108: 2897-2904 (1995).

Pardee, A.B., G1 Events and Regulation of Cell Proliferation, Science, 246: 603-608 (1989).

Pavletich et al., Crystal structure of the p27Kip1 cyclin-dependent-kinase inhibitor bound to the cyclin A-Cdk2 complex, Nature, 382(6589): 325-331 (1996).

Rossi et al., Understanding and modulating cyclin-dependent kinase inhibitor specificity: molecular modeling and biochemical evaluation of pyrazolopyrimidinones as CDK2/cyclin A and CDK4/cyclin D1 inhibitors, Comput. Aided Mol. Des., 19: 111-122 (2005).

Sausville, Complexities in the development of cyclin-dependent kinase inhibitor drugs, Trends Mol. Med., 8(4 Suppl.): S32-S37 (2002).

Schmitz et al., Limited Redundancy in Phosphorylation of Retinoblastoma Tumor Suppressor Protein by Cyclin-Dependent Kinases in Acute Lymphoblastic Leukemia, Am. J. Pathol., 169(3): 1074-1079 (2006).

Shapiro, G., Cyclin-Dependent Kinase Pathways as Targets for Cancer Treatment, J. Clin. Oncol., 24(11): 1770-1783 (2006).

Sherr, C.J., Mammalian G1 cyclins, Cell, 73: 1059-1065 (1993).

Sherr, C.J., Cancer Cell Cycles, Science, 274: 1672-1677 (1996).

Sherr et al., Living with or without cyclins and cyclin-dependent kinases, Genes & Development, 18: 2699-2711 (2004).

Sinhababu et al., Prodrugs of anticancer agents, Adv. Drug Delivery Rev., 19: 241-273 (1996).

Tan et al., Development and optimization of anti-HIV nucleoside analogs and prodrugs: A review of their cellular pharmacology, structure-activity relationships and pharmacokinetics, Adv. Drug Delivery Rev., 39: 117-151 (1999).

Tetsu et al., Proliferation of cancer cells despite CDK2 inhibition, Cancer Cell, 3(3): 233-245 (2003).

Wang et al., Hepatitis B virus integration in a cyclin A gene in a hepatocellular carcinoma, Nature, 343: 555-557 (1990).

Whittaker et al., The Cyclin-dependent Kinase Inhibitor CYC202 (R-Roscovitine) Inhibits Retinoblastoma Protein Phosphorylation, Causes Loss of Cyclin D1, and Activates the Mitogen-activated Protein Kinase Pathway, Cancer Res., 64: 262-272 (2004).

Zarkowska et al., Differential Phosphorylation of the Retinoblastoma Protein by G1/S Cyclin-dependent Kinases, J. Biol. Chem., 272(19): 12738-12746 (1997).

* cited by examiner

PYRAZOLOPYRIMIDINONE KINASE INHIBITOR

CROSS-REFERENCE TO RELATED APPLICATIONS

This application is a United States national stage filing under 35 U.S.C. §371 of international (PCT) application No. PCT/EP2008/056569, filed May 28, 2008 and designating the US, which claims priority to U.S. Prov. Appln. No. 60/932,155 filed May 29, 2007 and European application 07113226.0, filed Jul. 26, 2007.

FIELD OF THE INVENTION

The present invention provides a novel pyrazolo[3,4-d]pyrimidin-4-one, specifically a derivative of 1-(pyridin-4-yl)-pyrazolo[3,4-d]pyrimidin-4-one. This compound is a kinase inhibitor that shows unexpected anti-proliferative activity against cells, including against tumor cells, and anti-tumor activity in xenograft tumor models. The compound or a suitable salt or prodrug thereof is useful for the treatment of individuals suffering from a cancer or another proliferative disorder or disease.

BACKGROUND OF THE INVENTION

Kinases are important cellular enzymes that perform essential cellular functions such as regulating cell division and proliferation, and that appear to play a decisive role in many disease states such as in disease states that are characterized by uncontrolled proliferation and differentiation of cells. These disease states encompass a variety of cell types and maladies such as cancer, atherosclerosis, restenosis and other proliferative disorders.

One of the most important and fundamental processes in biology is the division of cells mediated by the cell cycle. This process ensures the controlled production of subsequent generations of cells with defined biological function. It is a highly regulated phenomenon and responds to a complex set of cellular signals both within the cell and from external sources. A complex network of tumor promoting and suppressing gene products are key components of this cellular signalling process. Over-expression of tumor-promoting components or the subsequent loss of the tumor-suppressing products will lead to unregulated cellular proliferation and the generation of tumors (Pardee, *Science* 246:603-608, 1989). Cyclin-dependent kinases (CDKs) play a key role in regulating the cell cycle machinery. They are complexes consisting of two components: a catalytic subunit (the kinase) and a regulatory subunit (the cyclin). To date, thirteen kinase subunits (cyclin-dependent kinases (CDKs) 1-13) have been identified in humans along with several regulatory subunits including cyclins (Cyc) A-H, K, L, N, and T, and CDK5, p35, and other proteins. Each kinase subunit can form pair(s) with one or several regulatory subunit partners, and in each case, such pair makes up the active catalytic moiety. Each transition of the cell cycle is regulated by a particular cyclin-dependent kinase complex: G1/S by CDK2/CycE, CDK4/CycD and CDK6/CycD; S/G2 by CDK2/CycA and CDK1/CycA; G2/M by CDK1/CycB (for review see Shapiro, *J. Clin. Oncol.* 24: 170ff, 2006). The coordinated activity of these kinase complexes guides the individual cells through the replication process and ensures the vitality of each subsequent generation (Sherr, *Cell* 73:1059-1065, 1993; Draetta, *Trends Biochem. Sci.* 15:378-382, 1990).

While experiments disrupting the genes encoding all three D-type cyclins, the two E-type cyclins, cyclin D-dependent CDK4 and CDK6, or cyclin E-dependent CDK2 in the mouse germ line showed that none of these genes is strictly essential for cell cycle progression (reviewed in Sherr and Roberts, *Genes & Development* 18: 2699-2711, 2004), an increasing body of evidence has shown a link between tumor development and cyclin-dependent kinase related malfunctions. Over-expression of the cyclin regulatory proteins and subsequent kinase hyperactivity have been linked to several types of cancers (Sherr C. J., *Science* 274:1672-1677, 1996; Jiang, *Proc. Natl. Acad. Sci. USA* 90:9026-9030, 1993; Wang, *Nature* 343:555-557, 1990). Indeed, human tumor development is commonly associated with alterations in either the CDK proteins themselves or their regulators (Cordon-Cardo C., *Am. J. Pathol.* 147:545-560, 1995; Karp J. E. and Broder S., *Nat. Med.* 1: 309-320, 1995; Hall M. et al., *Adv. Cancer Res.* 68:67-108, 1996). Endogenous, highly specific protein inhibitors of cyclin-dependent kinases were found to have a major effect on cellular proliferation (Kamb A., *Curr. Top. Microbiol. Immunol.* 227:139-148, 1998; Kamb et al., *Science* 264:436-440, 1994; Beach, *Nature* 336:701-704, 1993). These inhibitors include p16INK4 (an inhibitor of CDK4/CycD1), p21CIP1 (a general CDK inhibitor), and p27K1P1 (a specific CDK2/CycE inhibitor). A crystal structure of p27 bound to CDK2/CycA revealed how these proteins effectively inhibit the kinase activity through multiple interactions with the cyclin-dependent kinase complex (Pavletich, *Nature* 382:325-331, 1996). These protein inhibitors help to regulate the cell cycle through specific interactions with their corresponding cyclin-dependent kinase complexes. Cells deficient in these inhibitors are prone to unregulated growth and tumor formation.

In addition to the CDKs involved primarily in the core process of cell cycle progression (CDKs 1, 2, 4 and 6), other CDKs are responsible for regulating gene expression processes in the course of cell cycle progression. Specifically, CDK7 and CDK9 are known to phosphorylate the C-terminal domain of RNA Polymerase II and thereby drive the expression of anti-apoptotic proteins, D-type cyclins, and pro-angiogenesis factors (like hypoxia-induced VEGF). Therefore, also these so-called regulatory CDKs are attractive targets for therapeutic intervention (see Shapiro, *J. Clin. Oncol.* 24:1770ff, 2006).

Due to the clear connection between pharmacological CDK inhibition and cell cycle regulation, the potential use of CDK inhibitors in oncology was identified early on, and many small-molecule inhibitors belonging to different structural classes were identified (e.g., staurosporins, flavones (e.g., flavopiridol (see Shapiro, *J. Clin. Oncol.* 24:170ff, 2006)), purines (e.g., purvalanol; roscovitine (see Bach et al., *J. Biol. Chem.* 280: 31208ff, 1995)), pyrido[2,3-d]pyrimidinones, oxindoles, paullones, indenopyrazoles, anilinoquinazoline, aminothiazoles or diaryl ureas, and the first molecules are now undergoing clinical evaluation (for reviews see: Sausville, *Trends Mol. Med.* 8: S32-S37, 2002; Huwe et al., *Angew Chem Int Ed Engl.* 42: 2122-38, 2003; Fischer, *Cell Cycle* 3: 742-6, 2004; Fischer and Gianella-Borradori, *Expert Opin Investig Drugs* 14: 457-77, 2005).

Based on the current understanding of the biochemical roles of the CDKs 1, 2, 4 and 6, growth arrest can be expected in cells treated with inhibitors of these enzymes. Direct inhibition of CDK4/CycD and/or CDK6/CycD should arrest cells in G1 (Baughn et al., *Cancer Res.* 66: 7661-7, 2006). Moreover, indirect inhibition of CDK1 and CDK4 via downregulation of the corresponding cyclin partners through inhibiting the CDK-activating kinases CDK7 and/or CDK9, should also arrest cells in G1 (Whittaker et al., *Cancer Res.* 2004, 64, 262-72; Mateyak et al., *Mol Cell Biol.* 1999, 19, 4672-83). In principle, inhibition of CDK2 activity should result in arrest of cells in G1, however, it has been shown genetically in colon cancer cells that this block could be by-passed by CDK4 activity (Tetsu & McCormick, *Cancer Cell* 3: 233-45, 2003) Inhibition of CDK1/CycB should block exit from mitosis through inhibiting phosphorylation of components of the anaphase-promoting complex (Golan et al., *J Biol. Chem.* 277: 15552-7, 2002; Listovsky et al., *Exp Cell Res.* 255: 184-91, 2000), and it could also result in apoptosis through inhibiting the phosphorylation of Survivin (O'Connor et al., *Proc Natl Acad Sci USA.* 97: 13103-7, 2000).

In light of the above considerations a molecule with potent and balanced CDK inhibitory activities, particularly against CDK1, CDK2, CDK4, CDK6, CDK7 and CDK9, would be expected to be a promising candidate for the development of a cytostatic/cytotoxic drug in the therapy of cancer or other proliferative diseases (DePinto et al., *Mol. Cancer Ther.* 5: 2644-58, 2006; Joshi et al., *Mol. Cancer Ther.* 6: 918-25, 2007).

However, while CDK inhibitory activities, e.g., as determined in biochemical kinase inhibition assays in vitro, are highly important parameters for hit and lead identification in research, a successful development of a drug for therapeutic applications will finally depend on many additional factors, such as the in vitro ADMET profile (including solubility and permeability), cell biology studies (including cellular inhibition of disease-related cell lines), pharmacokinetic (including bioavailability) and pharmacodynamic studies (including, most importantly, activity in disease-related animal models), and the toxicological profile.

It is known that certain pyrazolo[3,4-d]pyrimidines, substituted in a specific manner, have pharmacologically useful properties. In particular, certain derivatives of pyrazolo[3,4-d]pyrimidin-4-ones are known to possess anti-proliferative activity (see, Rossi et al., *Comput. Aided Mol. Des.* 19: 111-22, 2005; Markwalder et al., *J. Med. Chem.* 47: 5894-911, 2004).

PCT publication WO 00/021926 broadly discloses a class of pyrazolo[3,4-d]pyrimidin-4-ones, including generic structures representing certain 1-phenyl- and 1-pyridyl-pyrazolo [3,4-d]pyrimidin-4-ones. However, no specific 1-pyridyl-substituted compounds are disclosed or their synthesis described, and no data are presented to indicate whether such compounds would exhibit inhibitory properties in, for example, CDK enzymatic assays. There is thus no particularized teaching to select pyridine substituents for producing pharmaceutically useful compounds, and, indeed, no demonstration that 1-pyridyl forms would be as effective as the compounds actually synthesized or effective at all in the disclosed uses. In particular, there is no teaching of the specific compound 1-(3,5-dichloropyridin-4-yl)-6-(3-hydroxy-4-pyrrolidinomethyl-phenyl)methyl-3-isopropyl-pyrazolo [3,4-d]pyrimidin-4-one (Compound I), disclosed below.

PCT publication WO 03/033499 specifically discloses certain 1-phenyl-3-isopropyl-6-arylmethyl-pyrazolo[3,4-d]pyrimidin-4-ones that are shown to inhibit cyclin-dependent kinases and to have certain activity in tumor models (see also WO 2004/092139; WO 2005/063765; see also, Caligiuri et al., *Chem Biol.* 12: 1103-15, 2005). Of note however, is that these applications do not specially disclose, generically claim or suggest a utility for any corresponding 1-pyridyl-pyrazolo [3,4-d]pyrimidin-4-ones. WO 2004/092139 and WO 2005/ 063765 both disclose 1-(2,6-dichlorophenyl)-6-(3-hydroxy-4-pyrrolidinomethyl-phenyl)methyl-3-isopropyl-pyrazolo [3,4-d]pyrimidin-4-one (P)

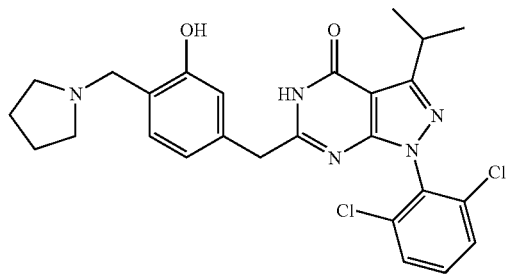

that can be shown to have balanced CDK inhibitory activities in biochemical kinase inhibition assays in vitro against CDK1, CDK2, CDK4, CDK6, CDK7 and CDK9. However, that compound did not have satisfactory properties in terms of solubility, permeability and particularly in xenograft tumor models in nude mice, so that further preclinical or clinical development for the treatment of cancer would not have been reasonably expected.

Thus, despite the progress that has been made, the search continues for low molecular weight kinase inhibitor compounds with balanced CDK inhibitory activities in biochemical kinase inhibition assays in vitro against CDK1, CDK2, CDK4, CDK6, CDK7 and CDK9, that show potent activity in a xenograft tumor model, and that are useful for treating cancer. Such compounds may additionally be useful for treating a wide variety of diseases, including cancer, tumors and other proliferative disorders or diseases including restenosis, angiogenesis, diabetic retinopathy, psoriasis, surgical adhesions, macular degeneration, and atherosclerosis. Thus, a strong need exists to provide compositions, pharmaceuticals and/or medicaments with kinase inhibitor activity or anti-proliferative activity against cells such as tumor cells. Such compositions, pharmaceuticals and/or medicaments may possess not only such activities, but may also exert tolerable, acceptable or diminished side effects in comparison to other kinase inhibitors or anti-proliferative agents. Furthermore, the spectrum of tumor types or other diseases responsive to treatment with such compositions, pharmaceuticals and/or medicaments may be broad. The active ingredients of such compositions, pharmaceuticals and/or medicaments may be suitable for use in the treatment of the mentioned indications as single agent, and/or in combination therapy, be it in connection with other therapeutic agents, with radiation, with operative/surgical procedures, thermal therapy or any other treatment known in the mentioned indications.

SUMMARY OF THE INVENTION

We have invented a novel pyrazolo[3,4-d]pyrimidin-4-one, specifically a derivative of 1-(pyridin-4-yl)-pyrazolo[3,4-d] pyrimidin-4-one having potent and balanced CDK inhibitory activities, particularly against CDK1, CDK2, CDK4, CDK6, CDK7 and CDK9, anti-proliferative activity against tumor cells, good pharmacokinetic and pharmacodynamic properties, including high solubility, permeability and oral bioavailability, and that exhibits surprisingly potent anti-proliferative activity in xenograft tumor models in nude mice, including in models using A2780 tumor cells. This compound shows promise as an effective therapeutic for diseases associated with CDK de-regulation or cellular proliferation, such as cancer, or other proliferative disorders or diseases, based on testing against established cancer cell lines and in vivo xenograft cancer models.

On the basis of comparative testing detailed below, the compound of the present invention is suitable for the treatment of individuals suffering from one or more forms of cancer or for the treatment of individuals suffering from one or more of a variety of other proliferative disorders and diseases.

The various aspects of the invention relate to the subject compound 1-(3,5-dichloropyridin-4-yl)-6-(3-hydroxy-4-pyrrolidinomethyl-phenyl)methyl-3-isopropyl-pyrazolo[3,4-d]pyrimidin-4-one, having the structure represented by formula (I) presented below, or the structure of any tautomeric form thereof. The subject compound may optionally be formed or used as a salt form, including a pharmaceutically acceptable salt. The subject compound is useful as a CDK inhibitor, showing anti-proliferative activity against cells, including against tumor cells, and anti-tumor activity in xenograft tumor models, and/or is useful for the treatment of individuals suffering from cancer or another proliferative disorder or disease.

In one aspect, the invention relates to pharmaceutical compositions, including a pharmaceutically acceptable diluent, excipient or carrier and an amount, such as a therapeutically effective amount, of such subject compound, e.g., which ameliorates the effects of cancer, or other proliferative disorders or diseases.

Another aspect of the invention relates to a packaged pharmaceutical product, including a pharmaceutical composition including the subject compound such as described above, and instructions which indicate that said pharmaceutical composition may be used for administration to a patient suffering from cancer, or another proliferative disorder or disease.

In another aspect, the invention relates to methods that involve administering to or contacting an individual, a cell, a tissue, an organ or an organism with an amount of, including a therapeutically effective amount, of the subject compound or of a pharmaceutical composition disclosed herein. These methods include, but are not limited to: killing, or inhibiting the proliferation or growth of, a cell (including of a tumor cell); treatment of an individual suffering from a disorder associated with the activity of one or more cyclin dependent kinases disclosed herein; treatment of an individual suffering from cancer; or the treatment of an individual suffering from another proliferative disorder or disease.

In another aspect, the invention relates to uses of the subject compound for the preparation of a medicament for the treatment of an individual suffering from cancer, or another proliferative disorder or disease.

Another aspect of the invention relates to a method of synthesizing 1-(3,5-dichloropyridin-4-yl)-6-(3-hydroxy-4-pyrrolidinomethyl-phenyl)methyl-3-isopropyl-pyrazolo[3,4-d]pyrimidin-4-one.

Accordingly, the present invention provides a subject compound that is (i) the compound of formula (I),

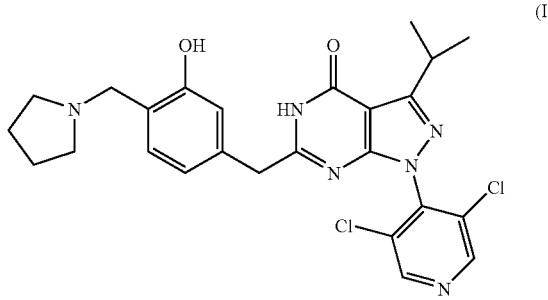

(ii) a tautomer of the compound of (i)

The invention further provides, any salt form of the subject compound, including any pharmaceutically acceptable salt, or any solvate of the subject compound, including any hydrate.

The invention further provides prodrug forms of the subject compound.

Other features and advantages of the invention will be apparent from the following detailed description and from the claims.

DETAILED DESCRIPTION OF THE INVENTION

Definitions

Figure 1:
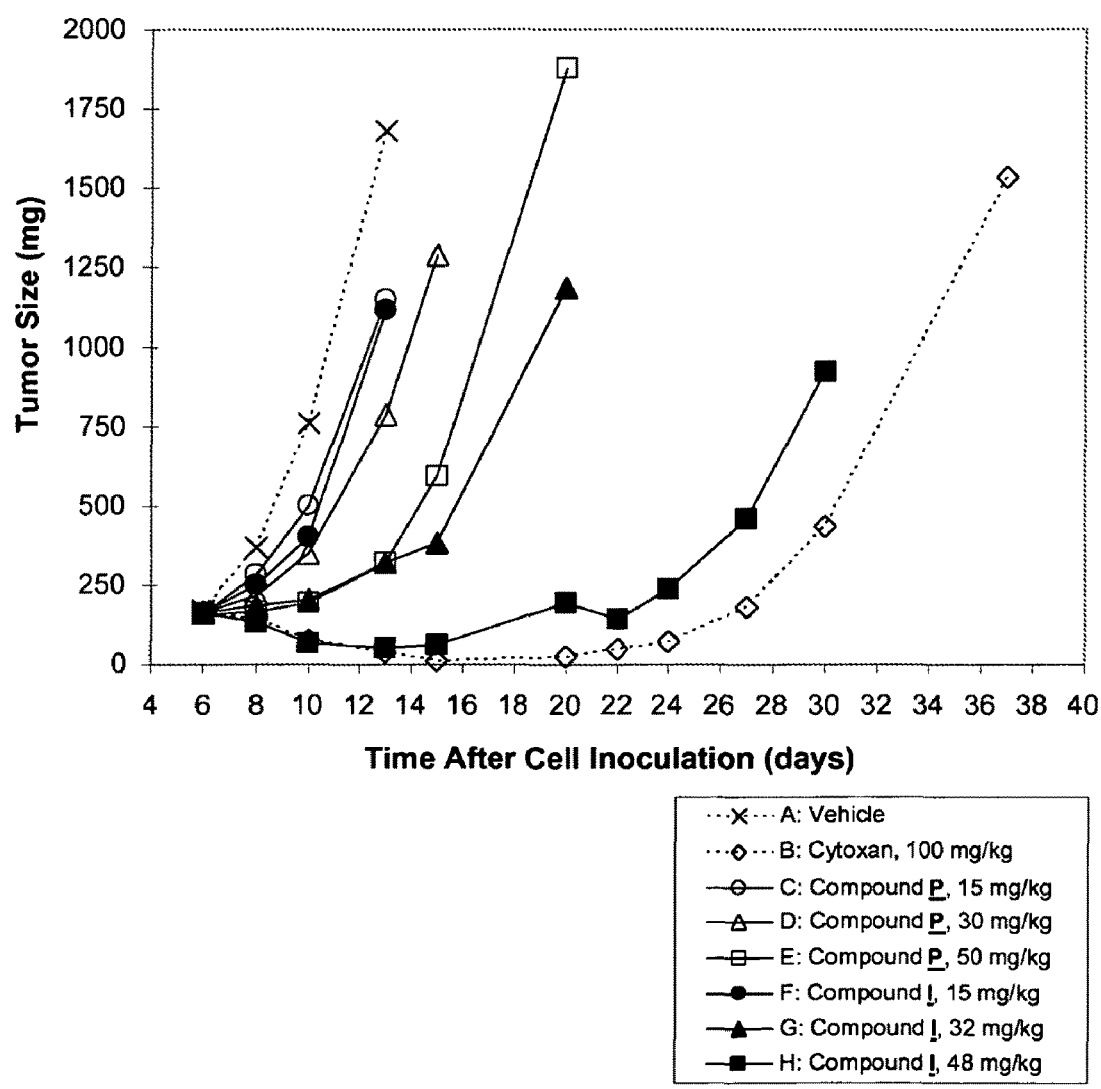
FIG. 1: Effects of twice-daily oral administration of Compound I or Compound P (and the controls Vehicle and Cytoxan) on: (a) A2780 ovarian xenograft tumor growth; and (b) mice body weight. Mean values for each group of mice is plotted at each time-point.
Figure 1:
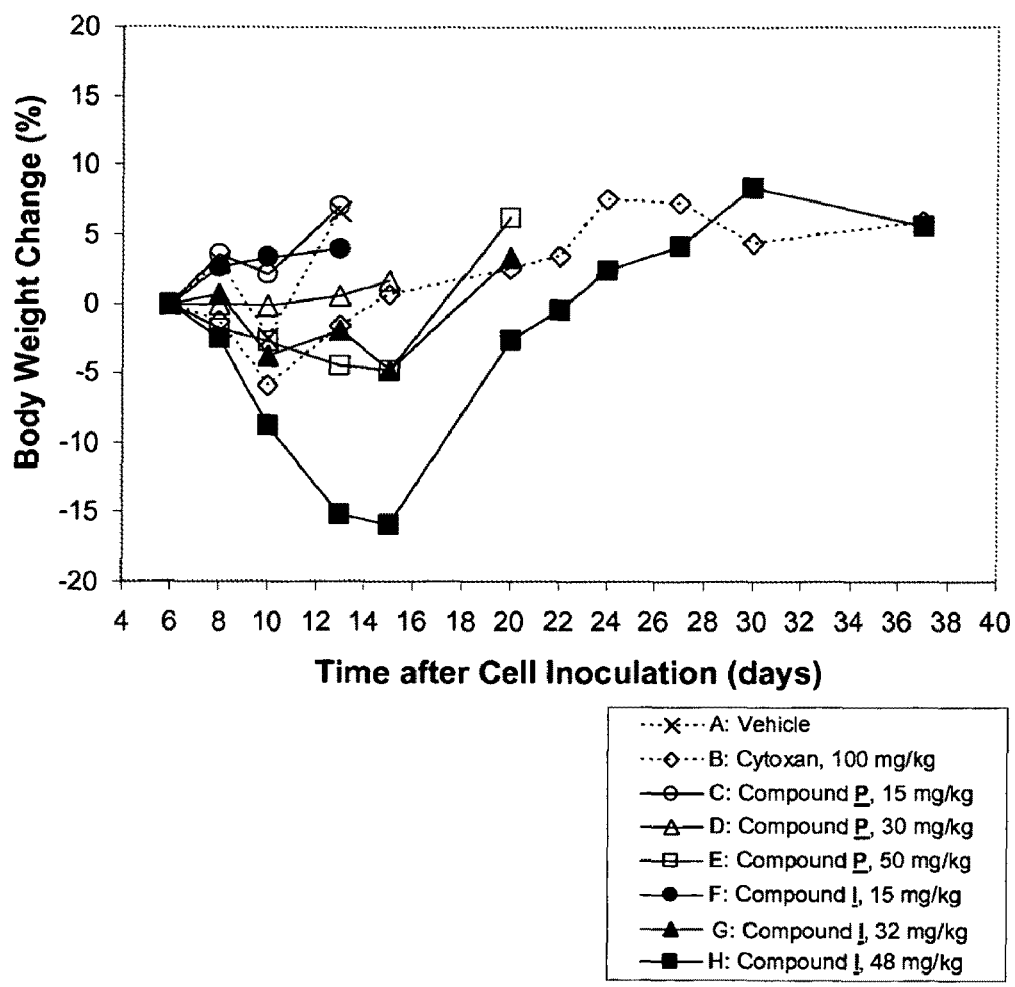

The term "tautomer" is art recognised, and describes an isomer of a given compound that results from the formal migration of a hydrogen atom or proton, accompanied by a switch of a single bond and adjacent double bond. As used herein the term tautomer includes any possible tautomeric form of the compound of the present invention of formula (I). It is further understood that different tautomeric forms of a compound may coexist in solution or in the solid state, e.g. in an equilibrium state, and that one tautomeric form may converted into a different tautomeric form over time. Thus, a reference to the compound of formula (I) is to be understood to refer to (i) the compound having the structure represented by formula (I), (ii) any tautomer of the compound of (i), or (iii) any mixture of the compound of (i) and any tautomer(s) thereof.

The term "isomer" refers to one of a set of compounds having identical molecular formulas but differing in the nature or sequence of bonding of their atoms or in the arrangement of their atoms in space.

The present invention is intended to include all isotopes of atoms occurring on the present compound. Isotopes are atoms having the same atomic number but different mass numbers. By way of general example and without limitation, isotopes of hydrogen include $^1H$, $^2H$ (deuterium) and $^3H$ (tritium). Isotopes of carbon include $^{12}C$ and $^{14}C$.

The term "active ingredient", as used herein, refers to an agent that is included in a pharmaceutical composition, and that is an active agent per se, or that results in the formation of an active agent such as, by way of non-limiting examples, an active ingredient being a prodrug, or an active ingredient that leads to the formation of a metabolite that is the active agent.

The term "active agent" refers to an agent that is responsible for, or is essentially contributing to, the desired activity, such as a therapeutic activity, of a method, such as a therapeutic method, using such agent, e.g., treatment of an individual upon administration of a pharmaceutical composition comprising an active ingredient. An active agent may exert its activity either alone or in combination with one or more additional active agents. The active agent may or may not be known, e.g., it may not be known whether an active ingredient acts directly or indirectly, such as an action mediated via a metabolite of the active ingredient. Without intending to be bound by a particular theory, it is believed that the compound of the present invention is an active agent as such.

The term "agent", as used herein, refers to any substance that exerts, or is supposed to exert, a certain activity in the setting described in the context where the term "agent" is used, either directly or indirectly.

The term "metabolite", as used herein, refers to any substance produced by metabolism or by a metabolic process. Metabolism, as used herein, refers to the various physical/chemical/biochemical/pharmacological reactions (each being a "metabolic process") involved in the transformation of a molecule or chemical compound occurring in the cell, tissue, system, or individual, including a human, that is contacted with such molecule or chemical compound.

The term "$IC_{50}$", as used herein, refers to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

As used herein, an "individual" means a multi-cellular organism, for example an animal such as a mammal, including a primate. In addition to primates, such as humans, a variety of other mammals can be comprised within the term individual. For example, other mammals including, but not limited to, cows, sheep, goats, horses, dogs, cats, guinea pigs, rabbits, rats, mice or other bovine, ovine, equine, canine, feline, or rodent species can be used.

As used herein, a "proliferative disorder" or a "proliferative disease" includes a disorder or disease that is characterized by proliferation of cells in an individual beyond or above normal levels, that is, above that level of proliferation of cells seen in normal, non-diseased cells of the same type. A proliferative disorder or disease may be caused or affected by changes in cellular growth, differentiation, or proliferation processes, including aberrantly regulated cellular growth, proliferation, differentiation, or migration of cells. Proliferation disorders or diseases include tumorigenic disorders or diseases. Examples of cellular growth or proliferation disorders include, but are not limited to tumors, cancer, autoimmune diseases, viral diseases, fungal diseases, neurodegenerative disorders and cardiovascular diseases. Cells included in, comprising or derived from a tumor or a cancer will generally be understood to be proliferating cells, typically hyper-proliferating cells, and in other circumstances, a tumor cell may be dysplastic, or may have proliferated.

As used herein, "cellular growth, differentiation or proliferation processes" are processes by which cells increase in number, size or content, by which a cell develops a specialized set of characteristics which differ from that of other cells, or by which a cell moves closer to or further from a particular location or stimulus, including amino acid transport and degradation and other metabolic processes of a cell.

As used herein, a "tumorigenic disorder or disease" includes a disorder or disease characterized by aberrantly regulated cellular growth, proliferation, differentiation, adhesion, or migration, which may result in the production of or tendency to produce tumors. As used herein, a "tumor" includes a benign or malignant mass of tissue, e.g. as formed by abnormal proliferation of cells.

As used herein, the term "anti-cancer agent" refers to an active agent having the ability to kill cancer cells in vivo or in vitro, to induce apoptosis in cancer cells, to inhibit (i.e., prevent, arrest, retard, slow, or delay) metastasis, or to otherwise exhibit anti-cancer activities. The term "anti-proliferative agent" refers to an active agent having the ability to inhibit proliferation of growing cells in vivo or in vitro, or to reduce the rate of cell division in proliferating or hyper-proliferating cells. Many agents are known to be anti-cancer agents and/or anti-proliferative agents, and such known agents include, but are not limited to, altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, cisplatin, oxaliplatin, picoplatin, LA-12, iproplatin, tetraplatin, lobaplatin, JM216, JM335, satraplatin, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, topotecan, irinotecan, 9-amino camptothecan, 9-nitro camptothecan, GS-211, JM 118, etoposide, teniposide, vinblastine, vincristine, vinorelbine, procarbazine, asparaginase, pegaspargase, octreotide, estramustine, and hydroxyurea. Said terms also include, but are not limited to, non-small molecule therapeutics, such as antibodies, e.g., 1D09C3 and other anti-HLA-DR antibodies as described in WO 01/87337 and WO 01/97338, Rituxan as described in U.S. Pat. Nos. 5,736,137, 5,776,456, 5,843,437, 4D5, Mab225, C225, Daclizumab (Zenapax), Antegren, CDP 870, CMB-401, MDX-33, MDX-220, MDX-477, CEA-CIDE, AHM, Vitaxin, 3622W94, Therex, 5G1.1, IDEC-131, HU-901, Mylotarg, Zamyl (SMART M195), MDX-210, Humicade, LymphoCIDE, ABX-EGF, 17-1A, Trastuzumab (Herceptin®, rhuMAb), Epratuzumab, Cetuximab (Erbitux), Pertuzumab (Omnitarg®, 2C4), R3, CDP860, Bevacizumab (Avastin®), tositumomab (Bexxar®), Ibritumomab tiuxetan (Zevalin®), M195, 1D10, Hu1D10 (Remitogen®, apolizumab), Danton/DN1924, an "HD" antibody such as HD4 or HD8, CAMPATH-1 and CAMPATH-1H or other variants, fragments, conjugates, derivatives and modifications thereof, or other equivalent compositions with improved or optimized properties, and proteins or peptides, e.g., those described in *Trends in Biotechnology* 21(12): 556-562, 2003.

The phrase "pharmaceutically acceptable" is art recognized, and is understood to refer to a property of a compound, material, composition, dosage form, etc. which property renders such compound, material, composition, dosage form, etc., suitable, within the scope of sound medical judgment, for administration to, or use in the pharmaceutical treatment of, an individual by providing a medically acceptable benefit/risk ratio. Such sound medical judgment should exclude, for example, that by bringing such compound, material, composition, dosage form, etc. in contact with the tissues of human beings or animals there is excessive toxicity, irritation, allergic response, or other problem or complication not commensurate with the benefits provided. Thus, "pharmaceutically acceptable" is used to refer to compounds, materials, compositions, dosage forms, etc. which, in the context of the utility for which they are employed (e.g., in the treatment of cancer or other proliferative disorders) are not biologically, chemically, or in any other way incompatible with body chemistry and physiology and also which do not unacceptably diminish the properties or potency of said compounds, materials, compositions, dosage forms, etc.

As used herein, the term "pharmaceutically acceptable salt" is art recognized, and is understood to refer to those derivatives of a parent compound wherein such parent compound is modified by making acid or base salts thereof, and where such salt is pharmaceutically acceptable. A pharmaceutically acceptable salt will usually maintain, or even improve on, the balance between the desired biological activity of an active ingredient and its undesired or toxicological effects.

Acid salts include salts from the reaction of mineral or organic acids with basic residues in the parent compound, such as amines. Non-limiting examples of suitable acid salts include those derived from inorganic acids, such as, for example, hydrochloric acid, hydrobromic acid, sulfuric acid, sulfamic acid, phosphoric acid, nitric acid, bicarbonic acid, carbonic acid; and acid salts formed with organic acids, such as, for example, formic acid, acetic acid, propionic acid, oxalic acid, glycolic acid, stearic acid, lactic acid, tartaric acid, succinic acid, malic acid, maleic acid, hydroxymaleic acid, malonic acid, ascorbic acid, citric acid, glutamic acid, benzoic acid, tannic acid, palmoic acid, alginic acid, phenylacetic acid, polyglutamic acid, salicylic acid, sulfanilic acid, 2-acetoxybenzoic acid, fumaric acid, toluenesulfonic, acid, methanesulfonic acid, ethane disulfonic acid, isethionic acid, naphthalenesulfonic acid, naphthalenedisulfonic acid, α-ketoglutaric acid, β-glycerophosphoric acid and polygalacturonic acid.

In particular embodiments of the various aspects of the invention, the salt form of the subject compound is a hydrochloride. In alternative embodiments of such aspects, the salt form of the subject compound is a maleate, including the particular embodiment of such salt comprising the subject compound and maleic acid in a 1:1 ratio.

Base salts include salts from the reaction of alkali metal or alkaline earth metal bases with acidic residues on the parent compound, such as carboxylic acids, phenolic residues, and the like. Suitable alkali metal or alkaline earth metal bases include lithium, potassium and sodium hydroxide, or calcium and magnesium hydroxide. Other suitable bases include those derived from metals such as zinc, bismuth, barium, or aluminum, and further include ammonia and organic amines, such as N,N-dibenzylethylene-diamine, D-glucosamine, or ethylenediamine. Moreover, suitable salts include those derived from a combination of acids and bases, such as, for example, a zinc tannate salt.

Pharmaceutically acceptable salts can be synthesized from the parent compound which contains a basic or acidic moiety by conventional chemical methods. Generally, such salts can be prepared by reacting the free acid or base forms of the compounds with a stoichiometric amount or a slight excess of the appropriate base or acid in water or in an organic solvent, or in a mixture of the two; generally, nonaqueous media like ether, EtOAc, ethanol, isopropanol, or acetonitrile are preferred. Lists of suitable salts are found in *Remington's Pharmaceutical Sciences,* 18th ed., Mack Publishing Company, Easton, Pa., 1990, p. 1445, the disclosure of which is hereby incorporated by reference.

Non-pharmaceutically acceptable acids and bases that find use, for example, in the synthesis and/or purification of a compound of interest are also contemplated herein. Thus, all "salts" of the compound of formula (I) are also encompassed within the scope of the instant invention.

The term "prodrug", as used herein, refers to an active ingredient that is converted into an active agent in one or more steps upon administration of a pharmaceutical composition including the prodrug. Generally speaking, prodrugs are derivatives of per se drugs that after administration to an individual, or to cells obtained from an individual, undergo conversion or metabolism to the physiologically active species, i.e. the active agent. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to finally result in the active agent. A prodrug may also be any covalently bonded carrier that releases an active agent in vivo when such carrier is administered as an active ingredient to an individual. Prodrugs can enhance numerous desirable qualities of pharmaceuticals (e.g., solubility, bioavailability, manufacturing, transport, pharmacodynamics, etc.). Prodrugs, for instance, may be bioavailable by oral administration even when the parent drug is not. Prodrugs may be prepared by modifying a functional group present in the parent compound in such a way that the modifications are reversible, for example in the course of administering the prodrug or in vivo, to result in the parent compound.

From among the voluminous scientific literature devoted to prodrugs in general, the following examples are cited: Gangwar et al., "Prodrug, molecular structure and percutaneous delivery", *Des. Biopharm. Prop. Prodrugs Analogs*, [Symp.] Meeting Date 1976, 409-21, (1977); Nathwani and Wood, "Penicillins: a current review of their clinical pharmacology and therapeutic use", *Drugs* 45(6): 866-94, 1993; Sinhababu and Thakker, "Prodrugs of anticancer agents", *Adv. Drug Delivery Rev.* 19(2): 241-273, 1996; Stella et al., "Prodrugs. Do they have advantages in clinical practice?", *Drugs* 29(5): 455-73, 1985; Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151, 1999; *Design of Prodrugs* (Bundgaard H. ed.), Elsevier Science Publishers B. V. (Biomedical Division) 1985, Chapter 1: Design of Prodrugs: Bioreversible derivatives for various functional groups and chemical entities (Hans Bundgaard); Bundgaard et al., *Int. J. of Pharmaceutics* (Elsevier) 22: 45-56, 1984; Bundgaard et al., *Int. J. of Pharmaceutics* (Elsevier) 29: 19-28, 1986; Bundgaard et al., *J. Med. Chem.* 32: 2503-2507, 1989; *Chem. Abstracts* 93: 137935y (Bundgaard et al.); *Chem. Abstracts* 95: 138493f (Bundgaard et al.); *Chem. Abstracts* 95: 138592n (Bundgaard et al.); *Chem. Abstracts* 110: 57664p (Alminger et al.); *Chem. Abstracts* 115: 64029s (Buur et al.); *Chem. Abstracts* 115: 189582y (Hansen et al.); *Chem. Abstracts* 117: 14347q (Bundgaard et al.); *Chem. Abstracts* 117: 55790x (Jensen et al.); and *Chem. Abstracts* 123: 17593b (Thomsen et al.).

The terms "administered", "administration", or "administering" a compound are art recognized and are understood to mean providing a compound to an individual, including a human, by bringing such individual in contact with, or otherwise exposing such individual to, such compound in such a manner that such compound has the opportunity to exert its activity, such as a therapeutic activity for the benefit of an individual suffering from a disease or disorder, or in need of treatment.

The term "in vitro" refers to a biological entity, a biological process, or a biological reaction outside the body in artificial conditions. For example a cell grown in vitro is to be understood as a cell grown in an environment outside the body, e.g., in a test tube, a culture tray, or a microtiter plate.

The term "therapeutically effective amount" is art recognized, and is understood to mean the amount of the subject compound that will elicit the biological, physiological, pharmacological, therapeutic or medical response of a cell, tissue, system, or individual, including a human, that is being sought by the practitioner administering said amount. In medical settings such desired results may include, e.g., lessening of the effects/symptoms of a disorder or disease, such as a proliferative disorder or disease, for example, a cancer or tumor, or killing or inhibiting growth of a proliferating cell, such as a tumor cell. The therapeutically effective amount can be determined by standard procedures, including those described below in the section "Dosages" herein.

The term "treatment" is art recognized, and shall include any one or more form of therapeutic intervention of a condition, such as any disorder or disease, of cells or of an individual, including therapeutic intervention at a symptom or associated-disorder of such condition, and further includes adjuvant therapy that is given after a substantial portion of the detectable or accessible manifestation of the condition, disorder or disease has undergone prior therapeutic intervention, e.g., by surgery. It is understood that a beneficial treatment may prevent onset of a disease or a symptom of it, may alleviate a disease or one or more symptoms or manifestations of it, may delay or inhibit the development or spread of a disease or one or more symptoms or manifestations of it, may cause regression of a disease or one or more symptoms or manifestations of it, or may cure a disease or eliminate one or more symptoms or manifestations of a disease. "Treatment" is not synonymous with "cure".

The term "further treated", "further administer", or "further administered" means that different active ingredients, therapeutic agents or compounds may be administered together, sequentially, alternatively, or intermittently. Such further administration may be temporally or spatially separated, for example, at different times, on different days, or via different modes or routes of administration.

Compound of the Present Invention

In certain embodiments, the compound of the invention, a salt form thereof (including a pharmaceutically acceptable salt), or a solvate form thereof (including a hydrate), is isolated. In certain embodiments, the compound of the invention, or a pharmaceutically acceptable salt thereof, is purified, e.g., to have a purity selected from: at least 80%, at least 90%, at least 95%, at least 97%, at least 98% and in certain embodiments at least 99%. Purity, as used herein, can refer to either absolute or relative purity. Absolute purity refers to the amount of compound of interest in relation to the total amount of a composition including such compound. Relative purity refers to the amount of a compound of interest in a composition relative to the amount of one or more other substances included in such composition, e.g. one or more impurities such as by-products, degradation products (e.g., metabolites, products of oxidation or hydrolysis, etc.) and/or compounds that degrade to form the compound of the invention (e.g., precursors or prodrugs). Such other substance(s) may, for example, be present in the product of a synthetic chemistry scheme for such compound of interest. Thus, absolute purity refers to the amount of the compound of interest relative to all others components of a composition including such compound, while relative purity is mainly used to describe purity with regard to closely related substances, and thus is unaffected by the addition of unrelated compounds, such as excipients, stabilizers, or other medicaments for conjoint administration. Purity can be assessed based upon weight, volume or molar ratios of one compound relative to others. Purity can be measured by a variety of analytical techniques, including elemental abundance, UV-visible spectrometry, HPLC, GC-MS, NMR, mass spectrometry, and thin layer chromatography. Preferred methods for determining the purity of compounds according to the invention are by HPLC, GC-MS, or NMR.

In certain embodiments, the compound of the invention, or a pharmaceutically acceptable salt thereof, is synthetically produced. The term "synthetically produced" refers to the generation of a compound using synthesis techniques well known to the skilled artisan with the aim of obtaining such compound.

In certain embodiments, the compound of the invention, a salt form thereof, including a pharmaceutically acceptable salt, or a solvate form thereof, including a hydrate, is in amorphous form.

In certain embodiments, the compound of the invention, a salt form thereof, including a pharmaceutically acceptable salt, or a solvate form thereof, including a hydrate, is in crystalline form.

Yet another aspect of the invention relates to prodrugs of the subject compound or a salt form thereof. Such prodrugs include compounds, wherein the hydroxyl group at the phenyl substituents or any nitrogen atom in the pyrrolidino group, the pyridine substituent or the pyrazolopyrimidone ring system of the compound of the present invention is bonded to any group that, when such prodrug is administered to cells, tissue, or an individual, including a human, is cleaved to form the free hydroxyl group or nitrogen atom, respectively. Examples of such prodrugs include, but are not limited to, acetate, formate, and benzoate derivatives of the phenolic hydroxy group in the compound of the present invention, or an N-acyloxyalkyl pyridinium derivative of the compound of the present invention (Davidsen et al., *J Med Chem.* 1994; 37:4423-9).

Formulations, Dosages and Applications

The present invention further provides a pharmaceutical composition including an active ingredient selected from: the subject compound, a salt form, such as a pharmaceutically acceptable salt, of the subject compound and a prodrug thereof; together with a pharmaceutically acceptable diluent, excipient or carrier, including pharmaceutical compositions including a therapeutically effective amount of such active ingredient.

Formulations

The compositions of this invention can be formulated and administered to treat cells, or an individual, such as a human, including an individual in need of treatment, such as an individual suffering from a disorder like a cancer. Such formulation and administration can be by any appropriate means that produces contact of the active agent with the active agent's site of action, such as a cell in the body of such individual, e.g., a cell included in a tumor or cancer present within such individual. They can be administered by any conventional means available for use in conjunction with pharmaceuticals, either as individual therapeutically active ingredients or in a combination of therapeutically active ingredients. They can be administered alone, but are generally administered with a pharmaceutically acceptable diluent, excipient or carrier selected on the basis of the chosen route of administration and standard pharmaceutical practice.

Pharmaceutical compositions for use in accordance with the present invention may be formulated in conventional manner using one or more pharmaceutically acceptable diluents, excipients or carriers. The pharmaceutical compositions of the invention can be formulated for a variety of routes of administration, including systemic and topical or localized administration. Techniques and formulations generally may be found in *Remington's Pharmaceutical Sciences*, Meade Publishing Co., Easton, Pa. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, capsules, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In certain embodiments, the pharmaceutical preparations may be non-pyrogenic, i.e., do not substantially elevate the body temperature of a patient.

In certain embodiments, the pharmaceutical compositions of the present invention are formulated for oral administration.

In certain other embodiments, the pharmaceutical compositions of the present invention are formulated for intravenous administration.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmaceutics. The amount of active ingredient which can be combined with a carrier material to produce a single dosage form will vary depending upon the individual being treated, as well as the particular mode of administration. The amount of active ingredient which can be combined with a carrier material to produce a single dosage form will generally be that amount of active ingredient which produces a therapeutic effect. Generally, out of one hundred percent, this amount will range from about 1 percent to about ninety-nine percent by weight of active ingredient, in certain embodiments from about 5 percent to about 70 percent by weight, and in particular such embodiments from about 10 percent to about 30 percent by weight.

Methods of preparing these formulations or compositions include the step of bringing into association the compound of the present invention, or a prodrug of such compound, with the carrier and, optionally, one or more accessory ingredients. In general, the formulations are prepared by uniformly and intimately bringing into association the compound of the present invention, or a prodrug of such compound, with liquid carriers, or finely divided solid carriers, or both, and then, if necessary, shaping the product.

For systemic administration, injection is preferred, including intramuscular, intravenous, intraperitoneal, and subcutaneous (i.m., i.v., i.p., and s.c., respectively). The phrases "systemic administration", "administered systemically", "peripheral administration", and "administered peripherally" as used herein mean the administration of a compound, drug or other material other than directly into the central nervous system, such that it enters the patient's circulatory system and, thus, is subject to metabolism and other like processes.

For injection, the pharmaceutical compositions of the invention can be formulated in liquid solutions, preferably in physiologically compatible buffers such as Hank's solution or Ringer's solution. In addition, the pharmaceutical compositions may be formulated in solid form and redissolved or suspended immediately prior to use. Lyophilized forms are also included.

Pharmaceutical compositions of the invention may be formulated to be suitable for oral administration and may take the form of capsules, cachets, sachets, pills, tablets, lozenges (using a flavored base, such as sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention, or a prodrug of such compound, as an active ingredient. The compound of the present invention, or a prodrug of such compound, may also be administered as a bolus, electuary or paste.

In formulating the pharmaceutical compositions of the invention in solid dosage forms for oral (p.o.) administration (capsules, tablets, pills, dragees, powders, granules and the like), the compound of the invention, a pharmaceutically acceptable salt thereof, or a prodrug of such compound, as active ingredient is mixed with one or more pharmaceutically acceptable carriers, such as sodium citrate or dicalcium phosphate, and/or any of the following, or combinations thereof: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, high molecular weight polyethylene glycols, and the like.

Gelatin capsules can contain the compound of the present invention, or a prodrug of such compound, as active ingredient and powdered carriers, such as lactose, starch, cellulose derivatives, magnesium stearate, stearic acid, and the like. Similar carriers can be used to make compressed tablets. Both tablets and capsules can be manufactured as sustained-release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract. Solid compositions of a similar type are also employed as fillers in soft and hard-filled gelatin capsules; preferred materials in this connection also include lactose or milk sugar as well as high molecular weight polyethylene glycols. A particular example of such formulation is a solution or suspension in an oil, for example olive oil, Miglyol, or Capmul, contained within a soft gelatin capsule. Antioxidants may be added to prevent long-term degradation as appropriate.

A tablet may be made by compression or molding, optionally with one or more ancillary ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulations so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or in certain embodiments, in a certain portion of the gastrointestinal tract, optionally in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the pharmaceutical compositions of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the pharmaceutical compositions for oral administration can also include adjuvants such as wetting agents, emulsifying and suspending agents, sweetening, flavoring, coloring, perfuming, and preservative agents.

Suspensions, in addition to the pharmaceutical composition of the present invention, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For buccal administration the pharmaceutical compositions may take the form of tablets or lozenges formulated in a conventional manner.

For administration by inhalation, the pharmaceutical compositions of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the therapeutic agents and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The pharmaceutical compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise the compound of the invention, a pharmaceutically acceptable salt thereof, or a prodrug of such compound, in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These pharmaceutical compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the pharmaceutical compositions. In addition, prolonged absorption of the injectable pharmaceutical form may be brought about by the inclusion of agents that delay absorption such as aluminum monostearate and/or gelatin.

In addition to the formulations described previously, the pharmaceutical compositions may also be formulated as a depot preparation. Such long acting formulations may be administered by implantation (for example subcutaneously or intramuscularly) or by intramuscular injection. Thus, for example, the pharmaceutical compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the pharmaceutical compositions of the invention are formulated into ointments, salves, gels, or creams as generally known in the art.

In some cases, in order to prolong the therapeutic effect of the compound of the invention, it is desirable to slow the absorption of the compound of the invention, a pharmaceutically acceptable salt thereof, or a prodrug of such compound, from subcutaneous or intramuscular injection. This may be accomplished by the use of a liquid suspension of crystalline or amorphous material having poor water solubility. The rate of absorption of the compound of the invention, a pharmaceutically acceptable salt thereof, or a prodrug of such compound, then depends upon its rate of dissolution which, in turn, may depend upon crystal size and crystalline form. Alternatively, delayed absorption of a parenterally administered inhibitor form is accomplished by dissolving or suspending the compound of the invention, a pharmaceutically acceptable salt thereof, or a prodrug of such compound, in an oil vehicle.

Pharmaceutical compositions of the invention may be formulated for rectal or vaginal administration as a suppository, which may be prepared by mixing the compound of the invention, a pharmaceutically acceptable salt thereof, or a prodrug of such compound, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredient.

Formulations of the pharmaceutical compositions of the present invention, which are suitable for vaginal administration, also include pessaries, tampons, creams, gels, pastes, foams or spray formulations containing such carriers as are known in the art to be appropriate.

Dosage forms for the topical or transdermal administration of the compound of this invention, or a prodrug of such compound, include powders, sprays, ointments, pastes, creams, lotions, gels, solutions, patches and inhalants. Such compound may be mixed under sterile conditions with a pharmaceutically acceptable carrier, and with any preservatives, buffers, or other adjuvant which may be required.

The ointments, pastes, creams and gels may contain, in addition to the compound of the invention, a pharmaceutically acceptable salt thereof, or a prodrug of such compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders can contain, in addition to the compound of this invention, or a prodrug of such compound, excipients such as lactose, talc, silicic acid, aluminum hydroxide, calcium silicates and polyamide powder, or mixtures of these substances.

Transdermal patches have the added advantage of providing controlled delivery of a compound of the present invention to the body. Such dosage forms can be made by dissolving or dispersing an inhibitor of the present invention in the proper medium. Absorption enhancers can also be used to increase the flux of the drug across the skin. The rate of such flux can be controlled by either providing a rate-controlling membrane or dispersing the compound of the present invention in a polymer matrix or gel.

Ophthalmic formulations, eye ointments, powders, solutions and the like, are also contemplated for use in this invention.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. In other embodiments, the pack or dispenser may be further packaged in an outer carton.

A pharmaceutical composition of the present invention can also be formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydroxypropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

Injectable depot forms can be made by forming microencapsulated matrices of the compound of the invention, a pharmaceutically acceptable salt thereof, or a prodrug of such compound, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations can also be prepared by entrapping the compound of the invention, a pharmaceutically acceptable salt thereof, or a prodrug of such compound, in liposomes or microemulsions that are compatible with body tissue.

Dosages

The dosage to be administered that will be a therapeutically effective amount of the compound sufficient, or reasonably expected by a health-care professional such as a physician, veterinarian, pharmacist or nurse, to result in amelioration of symptoms of, for example, the cancer or tumor will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

A dosage comprising a lower dose of the inventive compound, or of a salt or prodrug thereof, than would be therapeutically effective if administered alone may also be used, such as when the subject compound is used in combination with another therapeutically active agent, such as an anticancer agent, provided that such combination is therapeutically effective.

Toxicity and therapeutic efficacy of pharmaceutical compositions of the present invention can be determined by standard pharmaceutical procedures in cell cultures or experimental animals, e.g., for determining the $LD_{50}$ (the dose lethal to 50% of the tested population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical compositions that exhibit favourable therapeutic indices are useful for many circumstances. In certain circumstances, even pharmaceutical compositions that appear to exhibit debilitating or toxic side effects may be used, including circumstances where care is taken to design a delivery system that targets the active agent of such pharmaceutical compositions to the site of affected tissue in order to minimize potential damage to unaffected cells and, thereby, reduce or localize side effects.

The data obtained from cell culture assays and animal studies can be used in formulating a range of dosage for use in humans. In certain embodiments, the dosage lies within a range of circulating concentrations that include the $ED_{50}$ with little or no toxicity. The dosage may vary within this range depending upon the dosage form employed and the route of administration utilized. For the compound of the invention, any pharmaceutically acceptable salt thereof, or any prodrug of such compound, that is used in a method of the invention, the therapeutically effective dose can be estimated initially from cell culture assays. A dose may be formulated in animal models to achieve a circulating plasma concentration range that includes the $IC_{50}$ (i.e., the concentration of the test active ingredient which achieves a half-maximal inhibition of symptoms or inhibition of biochemical activity) as determined in cell culture. Such information can be used to more accurately determine useful doses in humans. Levels in plasma may be measured, for example, by high performance liquid chromatography.

It is understood that appropriate dosing of an active ingredient depends upon a number of factors known to those skilled in the art, e.g., a physician. The dose(s) of the active ingredient will vary, for example, depending upon the identity, size, and condition of the individual or sample being treated, further depending upon the route by which the composition is to be administered, if applicable, and the effect which the practitioner desires the therapeutic to have upon the therapeutic target of targets, such as cells, nucleic acid or polypeptides, through which the disease causes, symptoms or effects are mediated.

Exemplary doses include milligram or microgram amounts of the compound of the invention, a pharmaceutically acceptable salt thereof, or a prodrug of such compound, per kilogram of subject or sample weight, e.g., 1 microgram per kilogram to 500 milligrams per kilogram, 100 micrograms per kilogram to 50 milligrams per kilogram, or 1 milligram per kilogram to 5 milligrams per kilogram.

A person skilled in the art will appreciate that doses can also be calculated on a body surface basis. A person of 70 kg has an approximate body surface area of 1.8 square meter, and doses can be expressed as milligram or microgram amounts of the compound of the invention, a pharmaceutically acceptable salt thereof, or a prodrug of such compound, per body surface area of subject or sample, e.g., 50 microgram per square meter to 15 grams per square meter, 5 milligrams per square meter to 1.5 grams per square meter, or 50 milligram per square meter to 150 milligrams per square meter.

Applications

The present invention further provides the compound of the invention, a pharmaceutically acceptable salt thereof, or a prodrug of such compound, as for therapy.

In certain embodiments, said therapy is the treatment of an individual suffering from cancer, or another proliferative disorder or disease. In certain embodiments, said treatment is the treatment of an individual suffering from a disorder or disease, such as a cancer, associated with the activity of one or more cyclin dependent kinases, such as by inhibition of the activity of CDK1, CDK2, CDK4, CDK7, and/or CDK9.

Thus, the present invention additionally provides a method for treating an individual, such as a mammal, including a human, having or suffering from cancer or another proliferative disorder or disease, comprising administering to said individual an amount, such as a therapeutically effective amount, of the subject compound, a pharmaceutically acceptable salt thereof, or a prodrug thereof, or administering a pharmaceutical composition of the invention as described above. In certain embodiments, said individual is a human. In certain embodiments, said treatment is the treatment of a cancer that can be treated by the inhibition of the activity of one or more cyclin dependent kinases, such as the inhibition of the activity CDK1, CDK2, CDK4, CDK7, and/or CDK9.

In a further aspect, the invention provides methods of treating an individual suffering from a disease, such as a mammal, including a domestic mammal, rodent, and human, comprising the step of exposing or contacting said individual to an amount, including a therapeutically effective amount, of the subject compound, a pharmaceutically acceptable salt thereof, or a prodrug thereof. In certain embodiments, the disease is a cancer, or another proliferative disorder or disease. In certain embodiments, said individual is a human. In yet another embodiment, cells associated with said cancer, or said another proliferative disorder or disease, including tumor cells included in a tumor or a cancer (e.g. tumor cells that are malignant cell in an individual), are exposed to the subject compound, a pharmaceutically acceptable salt thereof, or a prodrug thereof. In certain embodiments, said compound, a pharmaceutically acceptable salt thereof, or a prodrug thereof, is administered to said individual in which said cells are present. In certain embodiments, said treatment is the treatment of a cancer that can be treated by the inhibition of the activity of one or more cyclin dependent kinases, such as the inhibition of the activity of CDK1, CDK2, CDK4, CDK7, and/or CDK9.

In a further aspect, the invention provides a method of killing or inhibiting proliferation or growth of cells, comprising contacting the cells with the compound of the invention, a pharmaceutically acceptable salt thereof, or a prodrug thereof. In one embodiment, the cells are contacted with such agent in vitro, while in an alternative embodiment the cells are present in an individual. In a particular embodiment the cells are cancer cells, for example cells from a tumor cell line or cells included in a tumor or cancer, including cancer cells from a tumor that can be treated by the inhibition of the activity of one or more cyclin dependent kinases, such as the inhibition of the activity of CDK1, CDK2, CDK4, CDK7, and/or CDK9.

Yet another aspect of the invention relates to the use of the compound as described above, a pharmaceutically acceptable salt thereof, or a prodrug thereof, for the preparation of a medicament for the treatment or prevention of a cancer, or of another proliferative disorder or disease including a cancer that can be treated by the inhibition of the activity of one or more cyclin dependent kinases, such as the inhibition of the activity of CDK1, CDK2, CDK4, CDK7, and/or CDK9. Additionally, the invention relates to a pharmaceutical composition comprising an active ingredient selected from: the compound as described above, a pharmaceutically acceptable salt thereof, and a prodrug thereof, together with a pharmaceutically acceptable diluent, excipient or carrier, where such pharmaceutical composition is for administration to an individual suffering from a disorder or disease such as a cancer, or of another proliferative disorder or disease, including a cancer that can be treated by the inhibition of the activity of one or more cyclin dependent kinases, such as the inhibition of the activity of CDK1, CDK2, CDK4, CDK7, and/or CDK9.

In yet another aspect, the invention relates to methods that involve contacting a cell, including a tumor cell, with an amount, such as a therapeutically effective amount, of the subject compound. These methods include the inhibition of the activity of one or more cyclin dependent kinases disclosed herein, such as a kinase selected from: CDK1, CDK2, CDK4, CDK7 and/or CDK9. In particular embodiments of such aspect, the kinase inhibited is CDK9. In certain embodiments, the cell is contacted with the subject compound in vitro, while in an alternative embodiment the cell is included in a tumor or a cancer present within an individual, such as a mammal including a human. Such individual many suffer from a proliferative disorder or disease, including a cancer or a disorder that can be treated by the inhibition of the activity of one or more cyclin dependent kinases, such as the inhibition of the activity of CDK1, CDK2, CDK4, CDK7, and/or CDK9.

In particular embodiments of the methods referred to in this section, such disorder or disease is associated with the activity of CDK9. In other embodiments, such disorder or disease is associated with the activity of CDK1, CDK2 and/or CDK4. In certain embodiments, said treatment leads to the inhibition of phosphorylation of a CDK substrate selected from: RNAPII, Rb and Eg-5; in cells. In certain embodiments, said inhibition of RNAPII phosphorylation is more pronounced than said inhibition of Rb and/or Eg-5 phosphorylation by a factor selected from: about 2-fold, about 5-fold, about 10-fold about 50-fold, and greater than 100-fold.

In certain treatment methods of the invention contemplated herein, tumors may be solid tumors, which are cancers of body tissues other than blood, bone marrow, or the lymphatic system. In other embodiments, tumors may be hematological tumors, such as leukemia and lymphomas. Leukemia is a collective term for malignant diseases characterized by a proliferation of malignantly changed white blood cells. Diseases arising from lymphatic tissue are called lymphomas.

Solid tumors may be selected from: liver cancer, stomach cancer, colon cancer, breast cancer, pancreas cancer, prostate cancer, skin cancer, renal cancer, bone cancer, thyroid cancer, skin cancer, including squamous cell carcinoma, esophagial cancer, kidney cancer, bladder cancer, gall cancer, cervical cancer, ovarian cancer, lung cancer (including bronchial, small and non-small-cell lung cancer), gastric cancer, and head and neck cancer.

Hematological tumors may be leukemia, such as Acute Myelogenous Leukemia (AML), Acute Lymphoblastic Leukemia (ALL), Acute Lymphocytic Leukemia, Acute Leukemia, Acute Promyelocytic Leukemia, Chronic Granulocytic Leukemia (CGL), Chronic Leukemia, Chronic Lymphocytic Leukemia (CLL), Chronic Myelogenous Leukemia (CML), Chronic Myelomonocytic Leukemia, Common-type Acute Lymphoblastic Leukemia, Eosinophilic Leukemia, Erythroleukemia, Extranodal Lymphoma, Follicular Lymphoma, Hairy Cell Leukemia, Monocytic Leukemia, Prolymphocytic Leukemia.

Hematological tumors may also be lymphoma, such as B Cell Lymphomas, Burkitt Lymphoma, Cutaneous T Cell Lymphoma, High-Grade Lymphoma, Hodgkin's Lymphoma, Non-Hodgkin's Lymphoma, Low-grade Lymphoma, Lymphoblastic Lymphoma, Mantle Cell Lymphoma, Marginal Zone Lymphoma, Mucosa-Associated Lymphoid Tissue (MALT) Lymphomas, T Cell Lymphomas, peripheral T cell lymphoma, multiple myeloma, Essential Thrombocythemia, Hairy Cell Lymphoma, Extramedullary Myeloma, Granulocytic Sarcomae.

Hematological tumors may also be tumors of myeloid lineage, including acute and chronic myelogenous leukemias, myelodysplastic syndrome, and promyelocytic leukaemia.

Tumors may also be of mesenchymal origin, such as fibrosarcoma and rhabdomyosarcoma. Furthermore, tumors may be tumors of the central and peripheral nervous system, such as astrocytoma, neuroblastoma, glioma, and schwannomas; and tumors may be other tumors, such as melanoma, seminoma, teratocarcinoma, osteosarcoma, xenoderoma pigmentosum, keratoctanthoma, thyroid follicular cancer, and Kaposi's sarcoma.

Tumors that are resistant or refractory to treatment with other anti-cancer or anti-proliferative agents may also benefit from treatment with the methods and pharmaceutical compositions of the present invention.

The compound disclosed herein may also be useful in inhibiting tumor angiogenesis and metastasis.

The compound of this invention, a pharmaceutically acceptable salt thereof, or a prodrug thereof, may also be useful in combination (administered together or sequentially) with known anti-cancer treatments such as radiation therapy or with other anti-cancer, anti-proliferative, cytostatic or cytotoxic agents. Other anti-cancer and anti-proliferative agents which may be used in combination with the compound of the present invention include those described herein. In combination treatment, the compound of the present invention, a pharmaceutically acceptable salt thereof, or a prodrug thereof, may be further administered with any other anti-cancer and anti-proliferative agent disclosed herein.

If formulated as a fixed dose, such combination products employ the compound of this invention, a pharmaceutically acceptable salt thereof, or a prodrug thereof, within the dosage range described herein and the other pharmaceutically active agent or treatment within its approved dosage range. Synergistic effects of drug combinations and effects on activity depending on order of administration are known in this field (see, e.g., *J. Cell Sci.*, 108: 2897, 1995; *Cancer Res.* 57: 3375, 1997), and optimizing dosage and order of delivery will be within the skill of practitioner in the art utilizing the compound of the present invention. The compound described herein, a pharmaceutically acceptable salt thereof, or a prodrug thereof, may also be administered sequentially with other anti-cancer or anti-proliferative agents when a combination formulation is inappropriate. In the absence of contrary indications, however, the invention is not limited in the sequence of administration; the compound described herein, a pharmaceutically acceptable salt thereof, or a prodrug thereof, may be administered either prior to, simultaneously with, or after administration of another anti-cancer or anti-proliferative agent. It is known, for example, that the cytotoxic activity of the cyclin-dependent kinase inhibitor flavopiridol is affected by the sequence of administration with anticancer agents (*Cancer Research*, 57, 3375, 1997).

Further Aspects of the Invention

Another aspect the invention provides a pharmaceutical package, wherein said package includes the compound of the present invention, a pharmaceutically acceptable salt thereof, or a prodrug thereof, or any pharmaceutical composition including such compound, pharmaceutically acceptable salt, or prodrug. In certain embodiments, the package comprises instructions which indicate that said pharmaceutical composition may be used for administration to an individual in need thereof, including a human, such as an individual suffering from a cancer or another proliferative disorder or disease. In certain other embodiments, the pharmaceutical package includes the compound of the present invention, a pharmaceutically acceptable salt thereof, or a prodrug thereof, formulated together with another pharmaceutical ingredient such as an anti-cancer or anti-proliferative agent. In this case, the compound of the present invention, a pharmaceutically acceptable salt thereof, or a prodrug thereof, and the other pharmaceutical ingredient may be formulated together or separately and in individual dosage amounts.

Other pharmaceutical ingredients that may be formulated together or separately with the compound of the present invention, a pharmaceutically acceptable salt thereof, or a prodrug thereof, include but are not limited to other anti-cancer and anti-proliferative agents such as described above. In certain still further embodiments, the pharmaceutical package comprises instructions to administer such active ingredient to an individual in need thereof. In yet another aspect the invention provides a pharmaceutical package for administration of a pharmaceutical composition to an individual suffering from a cancer, or from another proliferative disorder or disease, wherein said package includes at least the compound of the present invention, a pharmaceutically acceptable salt thereof, or a prodrug thereof. In certain still further embodiments, the pharmaceutical package comprises instructions to administer such pharmaceutical composition to an individual suffering from a cancer, or another proliferative disorder or disease.

As used herein the terms "pharmaceutical package" and "pharmaceutical pack" refer to any packaging system for storing and dispensing individual doses of medication for the treatment of an individual. Preferably the pharmaceutical package contains sufficient daily dosage units appropriate to the treatment period or in amounts which facilitate the individual's compliance with the regimen. In certain embodiments, the pharmaceutical pack comprises one or more vessels that include the active ingredient, e.g., the compound of the present invention. Such vessel can be a container such as a bottle, vial, syringe, or capsule, or may be a unit dosage form such as a pill. The active ingredient may be provided in the vessel in a pharmaceutically acceptable form or may be provided, for example, as a lyophilized powder. In further embodiments, the pharmaceutical pack may further include a solvent to prepare the pharmaceutical composition including such active ingredient for administration. In certain embodiments, the pharmaceutical composition including such active ingredient may be already provided in a delivery device, such as a syringe, or a suitable delivery device may be included in the pack. The pharmaceutical package may comprise pills, liquids, gels, tablets, dragees or the pharmaceutical preparation in any other suitable form. The package may contain any number of daily pharmaceutical dosage units. The package may be of any shape, and the unit dosage forms may be arranged in any pattern, such as circular, triangular, trapezoid, hexagonal or other patterns. One or more of the doses or subunits may be indicated, for example to aid the doctor, pharmacist or patient, by identifying such dose or subunits, such as by employing color-coding, labels, printing, embossing, scorings or patterns. The pharmaceutical package may also comprise instructions for the individual to be administered, the doctor, the pharmacist or any other person related to the act of administering the pharmaceutical composition to such individual.

Some embodiments comprise the administration of more than one active ingredient, including the compound as disclosed herein. Such administration may occur concurrently or sequentially. The active ingredients may be formulated together such that one administration delivers all components. Alternatively the active ingredients may be formulated separately. The pharmaceutical package may comprise the compound of the present invention and the other pharmaceutical ingredient in a single formulation, i.e., they are formulated together, or the compound of the present invention and the other pharmaceutical ingredient in individual formulations, i.e., they are formulated separately. Each formulation may comprise the compound of the present invention, a pharmaceutically acceptable salt thereof, or a prodrug thereof, and the other pharmaceutical ingredient(s) in individual dosage amounts (in approximately equal or unequal amounts). Administration of the compound of the present invention, a pharmaceutically acceptable salt thereof, or a prodrug thereof, and the other pharmaceutical ingredient(s) is typically such that a concentration results that is a therapeutically effective amount when in such combination.

As used herein, the term "instructions" means a product label, package insert and/or documents or other information describing relevant materials or methodologies pertaining to assembly, preparation or use of a kit or packaged pharmaceutical. These materials may include any combination of the following: background information, steps or procedures to follow for storage, preparation or administration, listing of components, indications for use, proposed dosages, warnings regarding possible side effects, instructions for administering the active ingredient(s), instructions in the case of overdose or ineffectiveness, technical support, and any other related documents. Instructions can be supplied in printed form, such as a package label or a package insert. Instructions for a packaged pharmaceutical or a pharmaceutical composition can be inserted in a delivery carton or finished package, e.g., as a package insert, and the text of such may require approval by a competent regulatory authority such as the Food and Drug Administration (FDA) of the United States. Alternatively or complementarily, instruction may also be stored in electronic form, e.g., on a computer-readable storage medium such as a computer-readable memory device, a centralized database, magnetic media such as hard disks, floppy disks, and magnetic tape; optical media such as compact discs, CD-ROMs and holographic devices; magneto-optical media such as floptical disks; and hardware devices that are specially configured to store and execute program code, such as application-specific integrated circuits (ASICs), programmable logic devices (PLDs) and ROM (read only memory) and RAM (random access memory) devices. Instructions may comprise a web address of an internet website from which more detailed instructions may be downloaded, or a recorded presentation. Instructions can contain one or multiple documents or future updates.

The invention further relates to a method of synthesizing a compound of claim 1 or optionally a salt thereof, comprising the step of reacting a compound having a structure represented by formula (II) with the compound having the structure represented by formula (III),

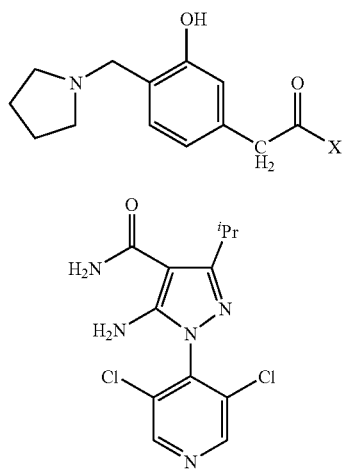

wherein X is selected from —O-alkyl, —O-alkenyl, —O-alkynyl, —O-acyl, and halogen; and, optionally, reacting the resultant compound with an acid to make an acid salt.

In a particular embodiment, X is —OEt.

The invention further relates to a method of synthesizing a pharmaceutically acceptable salt of the present invention, comprising the step of reacting the compound of the present invention with an acid. In a particular embodiment, the acid is hydrochloric acid. In another particular embodiment, the acid is maleic acid.

EXAMPLES

The subject compound was invented as described in Example A, and can be synthesized as shown in Examples B.1 to B.8. The surprising anti-proliferative activities of the compound according to the present invention in xenograft tumor models are demonstrated in Examples C.1 to C.5. Example D shows the potent inhibition of in-cell RNAPII phosphorylation by the subject compound.

Example A

Identification of the Compound of the Present Invention

WO 03/033499, WO 2004/092139; and WO 2005/063765 disclose a number of specific 1-phenyl-3-isopropyl-6-arylmethyl-pyrazolo[3,4-d]pyrimidin-4-ones, including, among other compounds, 1-(2,6-dichlorophenyl)-6-(3-hydroxy-4-pyrrolidinomethyl-phenyl)methyl-3-isopropyl-pyrazolo[3,4-d]pyrimidin-4-one (Compound P, see above).

A CDK inhibitor research program was established by us to find a novel compound with properties suitable for further development. In that program, a significant number of novel derivatives of pyrazolo[3,4-d]pyrimidin-4-ones were synthesized and examined, that were based on modifications of the substitution pattern as shown in Table 1:

TABLE 1

Derivation strategy

| Substituent Position | Number of different substituents tested | Examples |
|---|---|---|
| $R_1$ | ~8 | 2,6-dichlorophenyl; 2,4,6-trichlorophenyl; 3,5-dichloro-pyridin-4-yl |
| $R_2$ | ~18 | isopropyl; ethyl; cyclopropyl |
| M | ~5 | —$CH_2$— |
| $R_3$ | ~95 | 3-hydroxy-4-pyrrolidinomethylphenyl; 4-pyrrolidinomethylphenyl |

In total, more than 170 different such compounds were tested. However, in all but one case, the resulting compound did not show the desired parameter, or combination of parameters, and failed with respect to one or more of the properties as shown in Table 2, so that research on such compounds under the CDK inhibitor research program was halted.

TABLE 2

Derivation results

| Property | Failure rate | Comment on failure |
|---|---|---|
| in vitro CDK inhibition profile | >25% | $IC_{50}$ values for inhibition of CDK1, CDK2, CDK4, CDK6, CDK7 and/or CDK9 less potent that about 250 nM |
| Cellular inhibition profile | >30% | $IC_{50}$ values for inhibition of a set of model cell lines less potent than about 2 μM for one or more cell line |
| ADMET profile | >30% | e.g. lack of: metabolic stability, bioavailability, solubility, and/or permeability |
| In vivo xenograft model | >20% | >5% toxic; >15% inactive |
| Others | ~9% | ~7% decision made by analogy to other structurally closely related compounds that had failed, e.g., by observing toxicity that appeared to be related to a structural subclass; ~2% chemical instability |

Surprisingly, however, the subject compound, Compound I, showed significantly improved parameters for certain critical properties, and even maintained the desired parameters for other important properties, when compared to the closest structurally-related prior art compound, Compound P, as follows:

surprisingly, Compound I showed a significantly more potent activity in different xenograft tumor models, including an A2780 xenograft model using two different dosing regimens compared to Compound P (see Example C);

improved pharmacologically relevant ADMET parameter of permeability (about 70% permeability in a PAMPA assay at pH=7.4 for Compound I compared to about 57% for Compound P);

improved pharmacologically relevant ADMET parameter of solubility (about 390 μM at pH 7.4 for Compound I compared to about 210 μM for Compound P);

significant and improved inhibition of proliferation in a set of cancer-model cell lines, including cell lines A2780, HCT-116, HT-29, HepG2, NCI/ADR-RES, OVCAR3, H460, IMR-90, T98G, A549 among others, with $IC_{50}$ values for Compound I ranging between about 800 nM to about 10 nM (compared to $IC_{50}$ values for Compound P ranging between about 1.6 μM to about 16 nM);

significant and balanced CDK inhibitory activities in biochemical kinase inhibition assays in vitro against CDK1, CDK2, CDK4, CDK6, CDK7 and CDK9, as well as against CDK3 and CDK5, with $IC_{50}$ values for Compound I ranging from about 100 nM to about 2 nM that were comparable to those of Compound P (or even more potent for certain CDKs);

high specificity for CDKs with low inhibitory activity against a panel of non-CDK kinases;

The assays used for determining the properties of the kinase inhibitors were performed in accordance with standard procedures well known to those skilled in the art. For example, assays for determining inhibitory activity on CDKs or in cellular assays are described in WO 00/218962, WO 2005/026129, and WO 2005/063765. Solubility assays at pH 7.4 were essentially performed as described by Avdeef, A. in *Pharmacokinetic Optimization in Drug Research*; Testa, B.; van de Waterbeemd, H.; Folkers, G.; Guy, R. Eds.; Wiley-VHC: Zurich, 2001; pp 305-326. PAMPA permeability assays at pH 7.4 were essentially performed as described in Kansy et al., *J. Med. Chem.* 41: 1007-10, 1998.

Example B

Synthesis of 6-(3-Hydroxy-4-(pyrrolidinomethyl) phenylmethyl)-3-isopropyl-1-(3,5-dichloropyridin-4-yl)-pyrazolo[3,4-d]pyrimidin-4-one
(Examples B.1-B.7)

Examples B.1-B.8 show in detail the steps for the synthesis of 1-(3,5-dichloropyridin-4-yl)-6-(3-hydroxy-4-(pyrrolidinomethyl)phenylmethyl)-3-isopropyl-pyrazolo[3,4-d]pyrimidin-4-one (Compound I), and of salts thereof. A skilled artisan will appreciate that other routes of synthesis may be employed as well. In particular, other routes of synthesis may in fact be applied to certain aspects of the present invention. The skilled artisan is referred to general textbooks, such as March's *Advanced Organic Chemistry* (Michael B. Smith & Jerry March, Wiley-Interscience, 2000), *The Practice of Medicinal Chemistry* (Camile G. Wermuth, Academia Press, 2003) and *Protective Groups in Organic Synthesis* (Theosora W. Greene & Peter G. M. Wuts; John Wiley & Sons Inc., 1999).

Example B.1

Synthesis of (1-Hydroxy-2-methylpropylidene)methane-1,1-dicarbonitrile

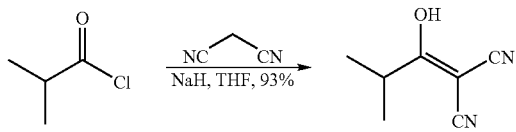

A solution of malononitrile (19.8 g, 300 mmole) in THF (150 mL) was added dropwise to a suspension of NaH (60% dispersion in oil, 24 g, 600 mmole) in THF (375 mL) at 0° C. The reaction was then warmed to room temperature and stirred for 1 hour. The suspension was then cooled to 0° C. and treated dropwise with a solution of isobutyryl chloride (31.4 mL, 299.7 mmole) in THF (125 mL). The addition was controlled so that the internal temperature did not rise above 10° C. Upon completion of the addition, the reaction was warmed to room temperature and stirred for 24 hours. The reaction was then quenched with $H_2O$ (50 mL) and concentrated under reduced pressure. The residue was then partitioned between EtOAc (500 mL) and 5% aq. HCl (300 mL). The aqueous layer was extracted with EtOAc (250 mL), and the combined organic layers were washed with brine (500 mL), dried, filtered, and concentrated under reduced pressure. The residue was partitioned between acetonitrile (300 mL) and hexanes (100 mL). The acetonitrile layer was washed with hexanes (100 mL), and evaporated to yield the desired product (38 g, 93% yield).

Example B.2

Synthesis of (1-Chloro-2-methylpropylidene)methane-1,1-dicarbonitrile

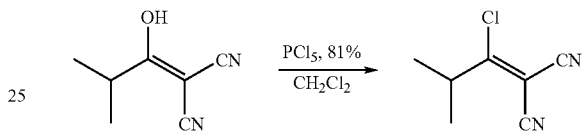

To a solution of (1-hydroxy-2-methylpropylidene)methane-1,1-dicarbonitrile (38 g, 279 mmole) in $CH_2Cl_2$ (600 mL) was added phosphorus pentachloride (63 g, 302 mmole). The reaction was stirred at room temperature for 16 hours. The reaction was then poured onto ice (500 g) and partitioned between $CH_2Cl_2$ (750 mL) and $H_2O$ (500 mL). The aqueous layer was extracted again with $CH_2Cl_2$ (500 mL), and the combined organic layers were washed with saturated aqueous $NaHCO_3$ (750 mL) and brine (750 mL). The organic layer was then dried ($MgSO_4$), filtered, and concentrated under reduced pressure to yield the desired chloride (35.6 g, 81% yield).

Example B.3

Synthesis of 5-Amino-1-(3,5-dichloropyridyl)-3-isopropyl-1H-pyrazole-4-carbonitrile

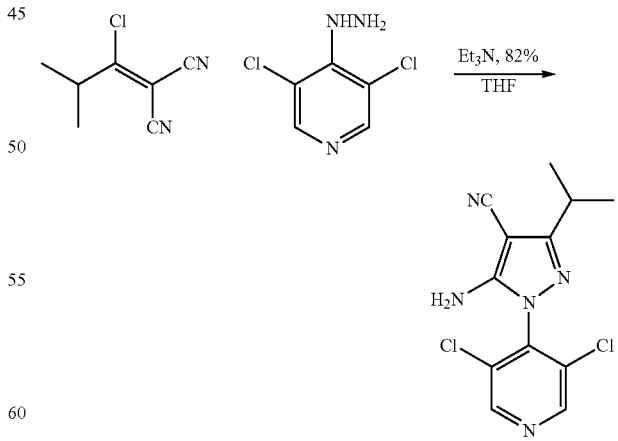

A solution of (1-chloro-2-methylpropylidene)methane-1, 1-dicarbonitrile (35.6 g, 230 mmole) in THF (875 mL) was treated with 3,5-dichloropyridylhydrazine (40.9 g, 230 mmole) followed by triethylamine (23 g, 230 mmole). The reaction was then heated to reflux for 18 hours. The reaction was then cooled to room temperature and partitioned between EtOAc (1 L) and 1M aqueous NaOH (500 mL). The aqueous layer was extracted with EtOAc (2×500 mL), and the combined organic layers were washed with 10% citric acid (500 mL), saturated aqueous NaHCO₃ (750 mL). The organic layer was dried (MgSO₄), filtered, and concentrated under reduced pressure to yield the desired product (56 g, 82% yield).

Example B.4

Synthesis of 5-Amino-1-(3,5-dichloropyridyl)-3-isopropyl-1H-pyrazole-4-carboxylic acid amide

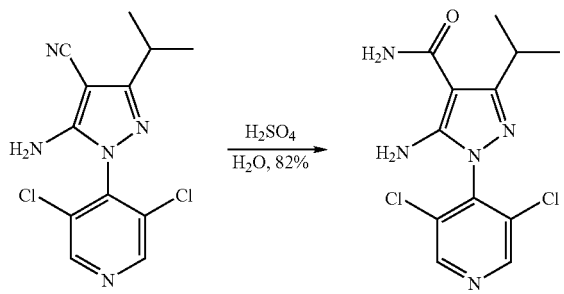

5-Amino-1-(3,5-dichloropyridyl)-3-isopropyl-1H-pyrazole-4-carbonitrile (56 g, 189 mmole) was taken up in concentrated H₂SO₄ (160 mL) and stirred at room temp for 16 hours. The reaction was then poured onto 3M aqueous NaOH (2 L) at 0° C. The resulting solid was then filtered and washed with H₂O (1 L). The product was then dried under vacuum to yield the desired amide (49 g, 82% yield).

Example B.5

Synthesis of 3-Hydroxyphenylacetic acid ethyl ester

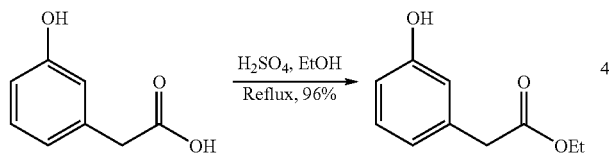

Concentrated H₂SO₄ (2 mL, 36 mmol) was added to a suspension of 3-hydroxyphenylacetic acid (25.9 g, 170 mmol) in EtOH (340 mL). The reaction mixture was heated at reflux for 4 hours then cooled to room temperature. The volatiles were removed in vacuo and the residue was suspended in EtOAc (300 mL). The organic layer was washed with saturated aqueous NaHCO₃ (1×150 mL), brine (1×150 mL), dried (anhydrous MgSO₄), and concentrated under reduced pressure to give the ester as a colorless oil (29.3 g, 96% yield).

Example B.6

Synthesis of 3-Hydroxy-4-(pyrrolidinomethyl)phenylacetic acid ethyl ester

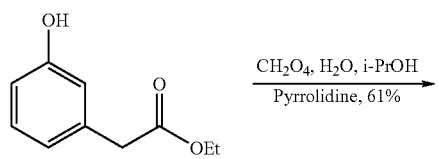

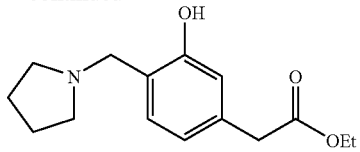

An aqueous solution of formaldehyde (37 wt. %, 2.47 g, 28 mmol) was added to a solution of ester (4.5 g, 25 mmol) and pyrrolidine (3.56 g, 50 mmol) in i-PrOH (50 mL). The reaction mixture was heated at reflux overnight. After cooling to room temperature the volatiles were removed in vacuo. The crude residue was purified by flash chromatography on silica gel eluting with CH₂Cl₂/MeOH (3-5%) containing 0.25% NH₄OH to give the benzyl amine as a colorless oil (5.5 g, 84% yield).

Example B.7

Synthesis of 6-(3-Hydroxy-4-(pyrrolidinomethyl)phenylmethyl)-3-isopropyl-1-(3,5-dichloropyridin-4-yl)-pyrazolo[3,4-d]pyrimidin-4-one (HCl Salt)

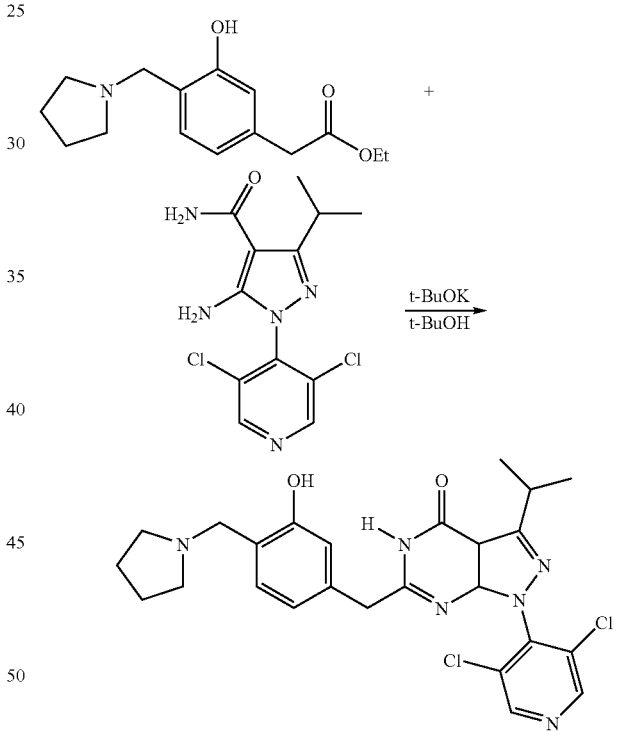

To a mixture of the ester (16.0 g, 60.0 mmol) and the pyrazole (6.28 g, 20.0 mmol) was added 120 mL of a 1M solution of potassium tert-butoxide (120.0 mmol) in tert-butyl alcohol. The resulting mixture was stirred at 80° C. for two hours and monitored by HPLC. The reaction mixture was cooled to room temperature and the tert-butyl alcohol was removed under reduced pressure.

To a mixture of the ester (17.66 g, 66.2 mmol) and the pyrazole (6.93 g, 22.05 mmol) was added 132.4 mL of a 1 M solution of potassium tert-butoxide (132.4 mmol) in tert-butyl alcohol. The resulting mixture was stirred at 80° C. for two hours and monitored by HPLC. The reaction mixture was cooled to room temperature, and tert-butyl alcohol was removed under reduced pressure.

The two reactions were combined and diluted with 500 mL of ethyl acetate. The organic layer was washed with a saturated, aqueous ammonium chloride solution. The organic layer was dried over sodium sulfate, filtered and concentrated under reduced pressure to give crude product. The crude material was purified via flash column chromatography eluting with 1.0-2.5% MeOH/CHCl$_3$/NH$_3$—H$_2$O (0.1%) (the gradient increase by 0.1%) to afford clean product. Added 100 mL of a 1M HCl solution in ether. Removed solvent and dried over vacuum to give 8.7 g of product (as the HCl salt) (38% yield).

Example B.8

Synthesis of 6-(3-Hydroxy-4-(pyrrolidinomethyl) phenylmethyl)-3-isopropyl-1-(3,5-dichloropyridin-4-yl)-pyrazolo[3,4-d]pyrimidin-4-one (Maleic Acid Salt)

6-(3-Hydroxy-4-(pyrrolidinomethyl)phenylmethyl)-3-isopropyl-1-(3,5-dichloropyridin-4-yl)-pyrazolo[3,4-d]pyrimidin-4-one (as free base, see Example B.7) was dissolved in isopropyl alcohol at 70° C., and a solution of maleic acid (1.05 equiv.) in isopropyl alcohol was added. The reaction mixture was stirred at 70° C. for 20 minutes, then cooled to RT overnight and filtered. The resulting solid was added to H$_2$O, the slurry stirred for 24 hours at RT and filtered. Melting point=209° C. (by differential scanning calorimetry); solubility: 2.5 µg/ml.

Example C

Activity of Compounds in Xenograft Tumor Models

The subject compound (Compound I) shows surprisingly significant anti-tumor activity in a number of in-vivo models of human cancers, and is surprisingly superior compared to a prior art compound (Compound P). This surprising activity was shown following oral administration of the compounds in a series of controlled murine xenograft experiments conducted as described below.

Methodology:

Xenograft Tumor-Models: 100 athymic nu/nu female mice (6-8 weeks old) from CRL were allowed to acclimate for 4 days. Cells for each respective tumor type (human A2780 ovarian tumor cells (ATCC), HCT116 colon carcinoma cells (ATCC) and H460 NSCLC (ATCC), as appropriate) were cultured in RPMI 1640 medium (Gibco) supplied with 15 mg/L of insulin, 10% FCS and 1% Pen/Strep. The 3$^{rd}$ passage of cells with approximate 90% confluence was used for these experiments. Briefly, on Day 0, mice were inoculated with 0.1 ml (total 5×10$^6$ cells) of the respective cell-type as a cell suspension (50×10$^6$ cells/ml) by subcutaneous injection into the fat pad area near the mammary gland under light anesthesia. When the average tumor weight in all mice reached over 100 mg (day 10), 80 animals with an average tumor size of 130 mg were selected and were randomly divided into 8 groups.

A 20 G gavage needle was used for the oral treatment. Formulation of each compound was as described in the results. The volume of administration was 0.2 ml per 20 g body weight except for the Cytoxan (cyclophosphamide) group (positive control) which was dosed i.p. as 0.1 ml per 20 g body weight.

Tumor growth and body weight were monitored and recorded three times a week. Tumors were measured by determining the length and width of the tumor with a digital caliper. Tumor weight was estimated using the following formula: Tumor Weight (mg)=(w$^2$×l)×0.52 where w=width and l=length in mm of the tumor. Tumor Growth Inhibition (TGI) % is calculated as follows: % TGI=100(1−T/C) where T is the mean tumor size of a compound treated group on a given day, and C is the mean tumor size of the vehicle control group on the same day.

Experimental treatment may cause partial regression (PR) or complete regression (CR) of tumors. PR is defined when the tumor size is 50% or less than the starting (day 1) size but greater than 0.0 mg for three consecutive measurements during the course of the study. CR occurs when there is no measurable tumor mass for three consecutive measurements. Cures are defined when CR are maintained until the completion of the experiment.

Mice were sacrificed when their tumors reached the 1000 mm$^3$ endpoint volume. Treatment efficacy was determined as Log Cell Kill (LCK). LCK is a calculation that determines the percentage of tumor cells that are presumably killed after the initiation of treatment and can be used as a quantitative measure of efficacy: LCK=(T−C)/(3.32)(Td) where T=the estimated time required for the treatment group of mice to reach 1000 mg tumor size, C=the estimated time for the control group tumors to reach 1000 mg in size, Td=the estimated Tumor Doubling time of the control group tumors during exponential growth and 3.32=the number of doublings required for a population to increase 1−log$_{10}$ unit. Each LCK unit represents 1−log$_{10}$ unit of cell killing (e.g., 1 LCK=90% kill, 2 LCK=99% kill, etc.).

Toxic deaths are defined as deaths caused by compound treatment and not by advanced disease state. A death is considered toxic if the animal dies within 2 weeks after the final compound treatment and the tumor size has not reached 1000 mg. Non-tumor related deaths after this point are recorded, but not considered toxic deaths.

Data analysis: The estimates and 95% confidence intervals for LCK were determined using a bootstrapping procedure. Briefly, the empirical distributions of T and Td were derived from B=1000 realisations of random selection of n individual animals with replacement from the set i=1, . . . , n of the appropriate group of mice containing n evaluable animals, estimating the mean tumor size for such selection of animals for each time-point, and linear regression analysis from a semi-log plot of such averages against time. Dead mice and mice with no measurable tumor size were treated as missing data and were ignored when calculating the average. The mean and standard deviation of the empirical distributions of the 1000 realisations were determined, from which a LCK estimate and 95% confidence intervals for such estimate were determined.

A non-parametric permutation test was used on certain pairwise comparisons of treatment groups (or treatment to control) in order to make a more precise test on the significance of any difference observed between two groups k and l. Briefly, the value $|T_k-T_l|$ is compared with the distribution of values $|T_k^{(b)}-T_l^{(b)}|$ that are obtained if the animals are randomly permuted between the two groups many times. $T_k$ is the estimated time for the group k of mice to reach 1000 mg in tumor size. If $|T_k-T_l|$ is larger than the 90$^{th}$ percentile of ($|T_k^{(b)}-T_l^{(b)}|$; b=1 . . . B), then the null hypothesis that $T_k=T_l$ can be rejected at a 10% confidence level.

Results:

Example C.1

Ovarian Cancer Model (A2780 Cell-Line)

Twice-Daily Oral Administration

A comparative trial was designed according to the protocol summarized in the following table, with the free-base equivalent dose indicated in square brackets. Compound P (as hydrochloric acid salt) was formulated in 30% PEG300/70% water, and Compound I (as hydrochloric acid salt) was formulated in 20% PEG300/80% D5W (5% dextrose water) and administered by oral gavage twice every day for 10 days (bid×10), while the Cytoxan control which was administered i.p. in saline every two days over a period of 10 days (q2 d×5):

| Group | Treatment | N | Dose (mg/kg, po) | Schedule |
|---|---|---|---|---|
| A | Vehicle (30% PEG300/70% water) | 10 | — | bidx10 |
| B | Cytoxan | 10 | 100, ip | q2dx5 |
| C | Compound P | 10 | 15 [14] | bidx10 |
| D | Compound P | 10 | 30 [28] | bidx10 |
| E | Compound P | 10 | 50 [47] | bidx10 |
| F | Compound I | 10 | 15 [14] | bidx10 |
| G | Compound I | 10 | 32 [30] | bidx10 |
| H | Compound I | 10 | 48 [45] | bidx10 |

The in vivo doubling time of the A2780 cells in this experiment was estimated as 2.1 days. Representative data are shown in FIG. 1, and summary results are tabulated below:

| Group | Treatment | Max % BW Loss (d) | Toxic Mortality | PR | CR | Cure | Max % TGI (d) | LCK ± CI (95%) ($T_d$: 2.1 d) |
|---|---|---|---|---|---|---|---|---|
| B | Cytoxan | 5.9 (10) | 0 | 5 | 5 | 0 | 98 (13) | 3.56 ± 0.43 |
| C | P-15 mg | 0 (6) | 0 | | | | 34 (10) | 0.20 ± 0.16 |
| D | P-30 mg | 0.1 (10) | 0 | | | | 54 (10) | 0.44 ± 0.19 |
| E | P-50 mg | 4.7 (15) | 0 | | | | 81 (13) | 1.06 ± 0.48 |
| F | I-15 mg | 0 (6) | 0 | | | | 47 (10) | 0.29 ± 0.23 |
| G | I-32 mg | 4.8 (15) | 0 | | | | 81 (13) | 1.72 ± 0.89 |
| H | I-48 mg | 15.9 (15) | 0 | 5 | 1 | 3 | 97 (13) | 3.38 ± 0.81 |

Figure 2:
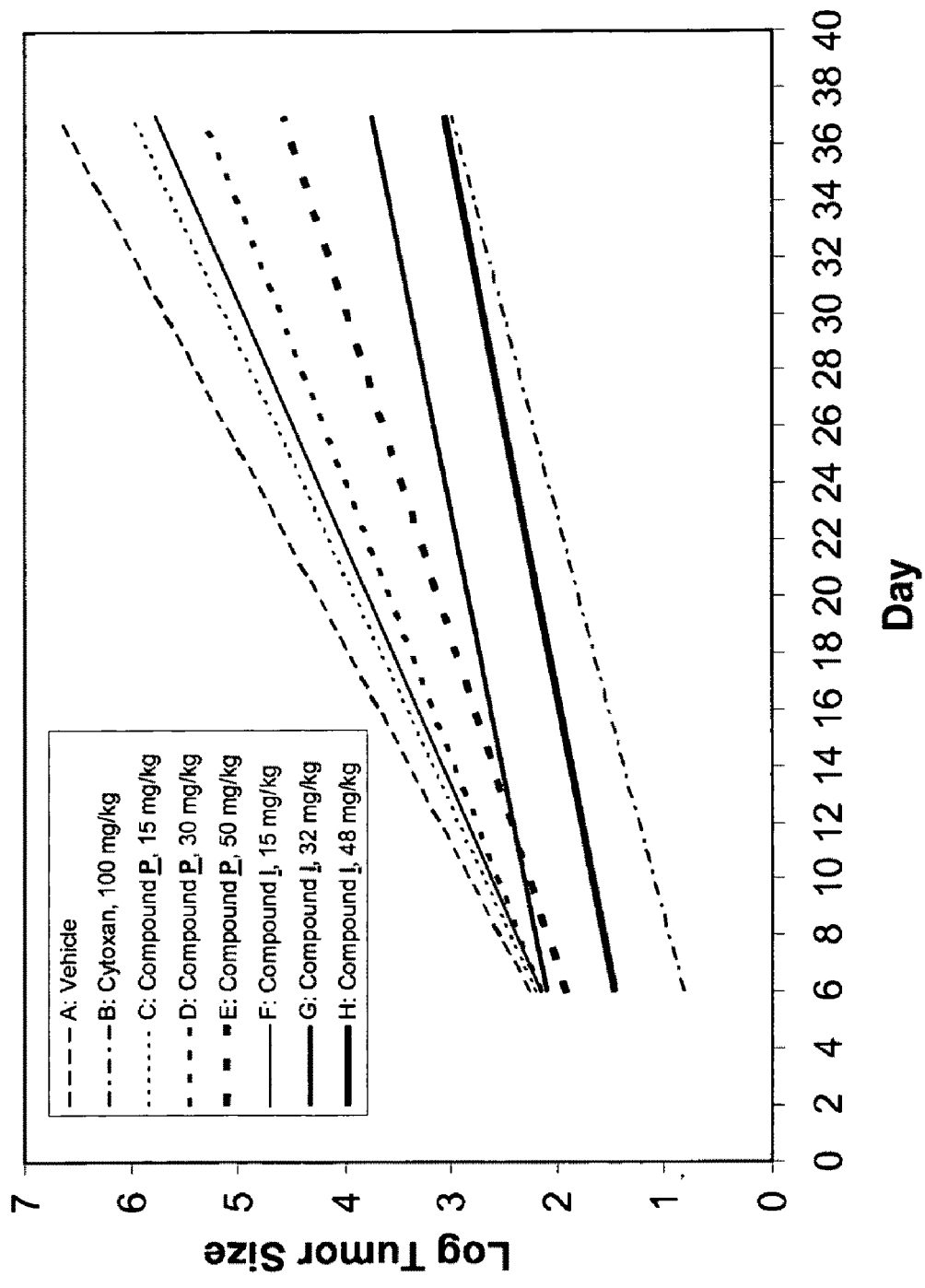
FIG. 2: Fitted values following linear-regression on log-linear plotted data for various groups of mice inoculated with A2780 cells and administered Compound P, Compound I, Vehicle or Cytoxan.

The surprising increase in anti-tumor activity of Compound I is shown by a LCK for a treatment group that is in each case larger than that for the group treated with a corresponding dose of Compound P. A log-linear plot of the fitted values following linear regression is shown in FIG. 2, which further demonstrates the surprising increased efficacy of Compound I over Compound P. In terms of individual mice, at the highest dose of Compound I, not only were partial and complete responses of tumor growth seen, but a number of individual mice were totally cured. That is, the subject compound (unlike the prior-art compound or even the positive control), was able to reduce the size of the tumor below a detectable level for the entire duration of the experiment.

Indeed, pair-wise analysis of certain groups of mice by permutation test, to test whether the null-hypothesis of their being no difference in activity between two groups could be rejected—i.e., there being a significant difference in the groups' LCK taking into account the variability actually observed in the experiment (see below), showed that Compound I showed a highly significant increased activity over Compound P (except for the lowest dosage for which no significant difference was observed, although even at this low dosage, Compound I was significantly active compared to the control group A). Even more surprising was that at the highest dose (group H), Compound I was equivalently as highly active as the positive control Cytoxan (group B), and that the highest dose of Compound P (group E) had a lower LCK than that of the medium dose of Compound I (group G), although the sensitivity of the test was unable to reject the null-hypothesis at this level of significance.

| Groups | Comparison | LCK estimates | Permutation Test p-Value | p < 0.10 |
|---|---|---|---|---|
| C-F | P-15 vs I-15 | 0.20 vs 0.29 | 0.418 | — |
| D-G | P-30 vs I-32 | 0.44 vs 1.72 | 0.008 | reject |
| E-H | P-50 vs I-48 | 1.06 vs 3.38 | 0.035 | reject |
| A-F | Vehicle vs I-15 | 0.0 vs 0.29 | 0.003 | reject |
| B-H | Cytoxan vs I-50 | 3.56 vs 3.38 | 0.550 | — |
| E-G | P-50 vs I-32 | 1.06 vs 1.72 | 0.180 | — |

Example C.2

Ovarian Cancer Model (A2780 Cell-Line)

Daily Oral Administration

A comparative trial was designed having the protocol summarized in the following table, with the free-base equivalent dose indicated in square brackets. Compound I and Compound P were formulated as above, and were administered p.o. every day for 10 days (qd×10). Mice in Group B were administered with a compound known as R547 (DePinto et al., *Mol. Cancer Ther.* 5: 2644-2658, 2006) formulated in 20% DMA/30% PEG 300/50% water.

| Groups | Treatment | N | Dose (mg/kg, po) | Schedule |
|---|---|---|---|---|
| A | Vehicle (20% DMA/30% PEG 300/50% water) | 10 | — | qdx10 |
| B | R547 | 10 | 100 | qdx1* |
| C | Compound P | 10 | 40 [37] | qdx10 |
| D | Compound P | 10 | 70 [65] | qdx10 |
| E | Compound P | 10 | 100 [93] | qdx9** |
| F | Compound I | 10 | 32 [30] | qdx10 |
| G | Compound I | 10 | 63 [59] | qdx10 |
| H | Compound I | 10 | 95 [89] | qdx7*** |

Notes:

*the schedule was originally as qdx10, but 5/10 mice died after the 1st dose

**one mouse died after the 9th dose

***one mouse died after the 7th dose

Figure 3:
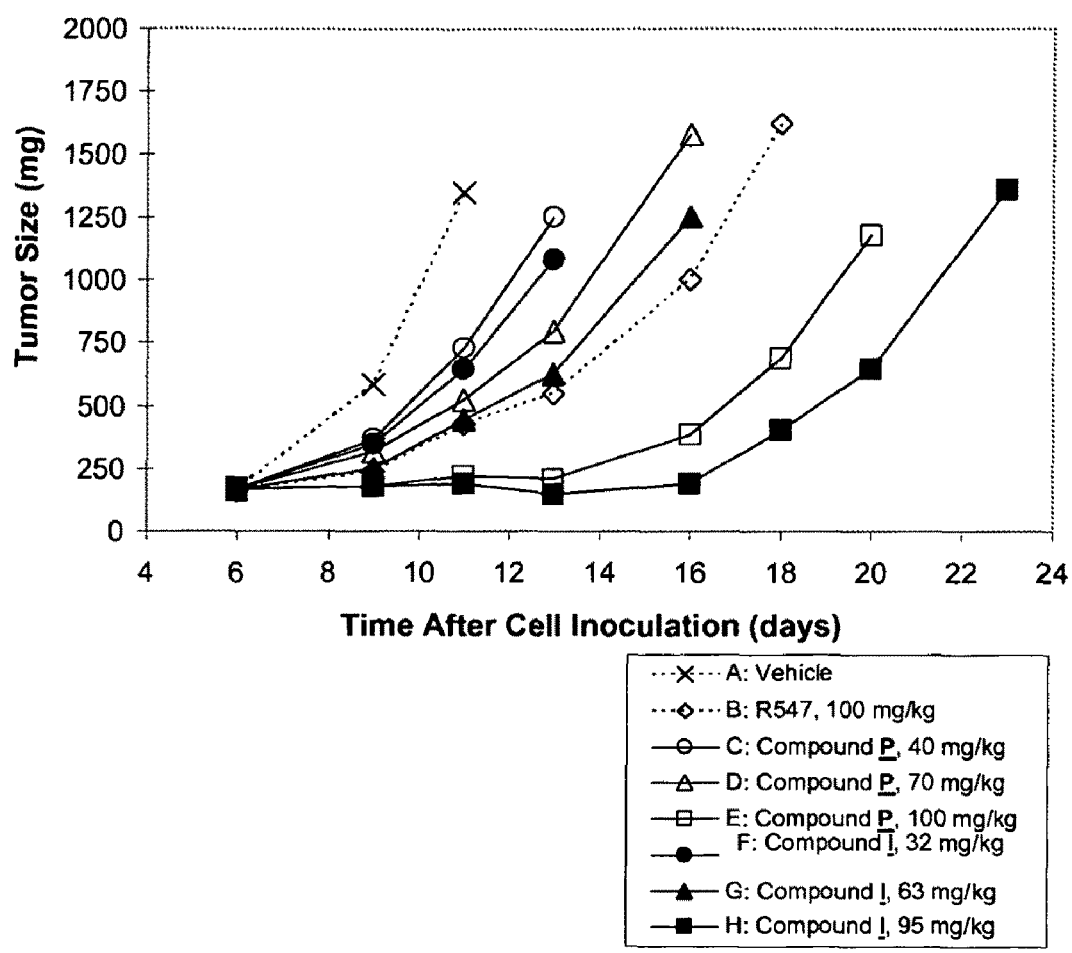
FIG. 3: Effects of daily oral administration of Compound I or Compound P (and the controls Vehicle and R547) on: (a) A2780 ovarian xenograft tumor growth; and (b) mice body weight. Mean values for each group of mice is plotted at each time-point.
Figure 3:
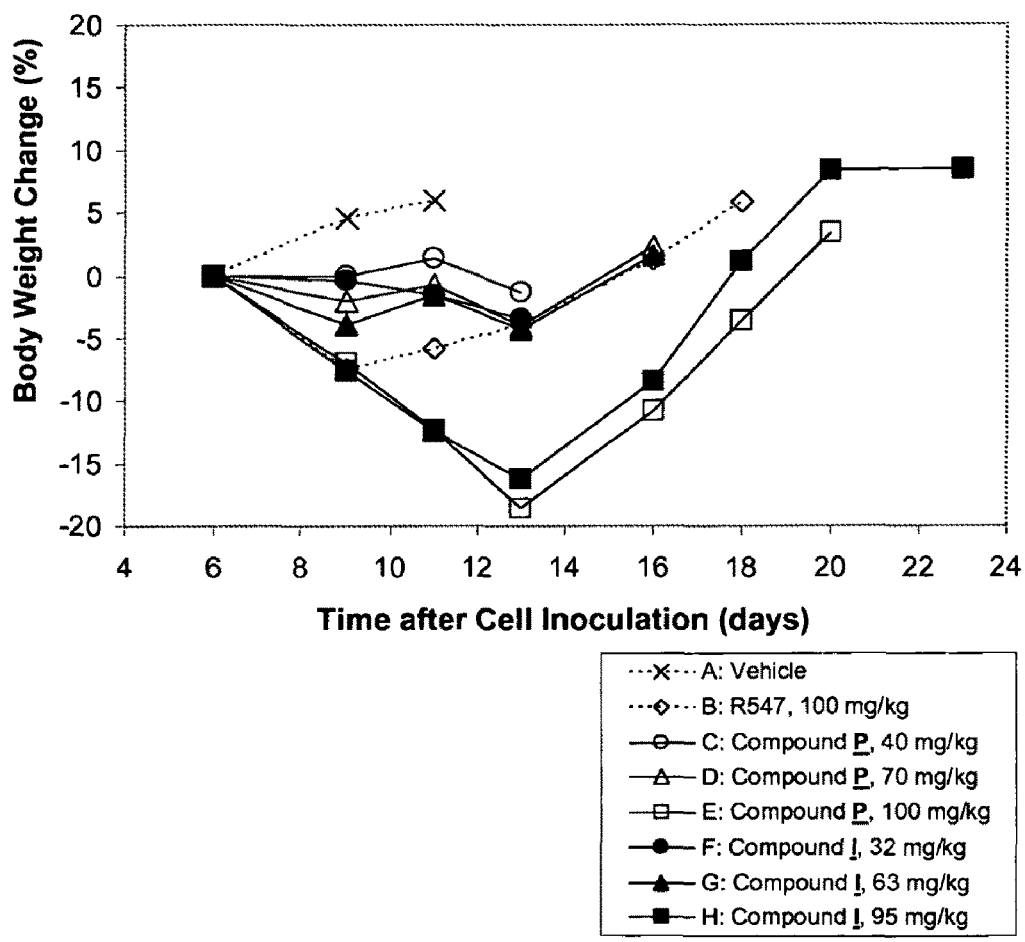

The in vivo doubling time of the A2780 cells in this experiment was estimated as 1.7 days. Representative data are shown in FIG. 3, and summary results are tabulated below:

| Group | Treatment | Max % BW Loss (d) | Toxic Mortality | Max % TGI (d) | LCK ± CI (95%) ($T_d$: 1.7 d) |
|---|---|---|---|---|---|
| B | R547 | 7.5 (9) | 5/10 | 68.5 (11) | 1.05 ± 0.56 |
| C | P-40 mg | 1.3 (13) | 0 | 46.2 (11) | 0.34 ± 0.21 |
| D | P-70 mg | 4.1 (13) | 0 | 61.1 (11) | 0.75 ± 0.46 |
| E | P-100 mg | 18.6 (13) | 1/10 | 83.9 (11) | 1.78 ± 0.56 |
| F | I-32 mg | 3.5 (13) | 0 | 52.2 (11) | 0.44 ± 0.24 |
| G | I-63 mg | 4.3 (13) | 0 | 67.3 (11) | 0.93 ± 0.39 |
| H | I-95 mg | 16.3 (13) | 1/10 | 86.2 (11) | 2.16 ± 0.44 |

Compound I shows a general increase in anti-tumor activity, as estimated by LCK, for each dose as compared to the corresponding dose of Compound P. Pair-wise analysis of certain groups of mice by permutation test (see below) showed that Compound I showed a significantly increased activity over Compound P at the highest dosage, while the generally observed superiority of Compound I over Compound P could not be significantly concluded using this stringent test, which was not able to reject the null-hypothesis at this level of significance for the 2 lower dosages.

| Groups | Comparison | LCK estimates | Permutation Test p-Value | p < 0.10 |
|---|---|---|---|---|
| C-F | P-40 vs I-32 | 0.34 vs 0.44 | 0.322 | — |
| D-G | P-70 vs I-63 | 0.75 vs 0.93 | 0.423 | — |
| E-H | P-100 vs I-95 | 1.78 vs 2.16 | 0.068 | reject |

Example C.3

Lung Cancer Model (H460 Cell-Line)

Daily Oral Administration

The study design is shown in the following table, with the free-base equivalent dose indicated in square brackets. Compound I and Compound P were formulated as above, and were administered p.o. every day for 10 days (qd×10). Mice in Group B were administered R547 (formulated as above) every two days over 10 days (q2 d×5).

| Group | Treatment | N | Dose (mg/kg, po) | Schedule |
|---|---|---|---|---|
| A | Vehicle (30% PEG300/70% water) | 10 | — | qdx10 |
| B | R547 | 10 | 40 | q2dx5 |
| C | Compound P | 10 | 40 [37] | qdx10 |
| D | Compound P | 10 | 70 [65] | qdx10 |
| E | Compound P | 10 | 100 [93] | qdx10 |
| F | Compound I | 10 | 32 [30] | qdx10 |
| G | Compound I | 10 | 63 [59] | qdx10 |
| H | Compound I | 10 | 95 [89] | qdx10 |

Figure 4:
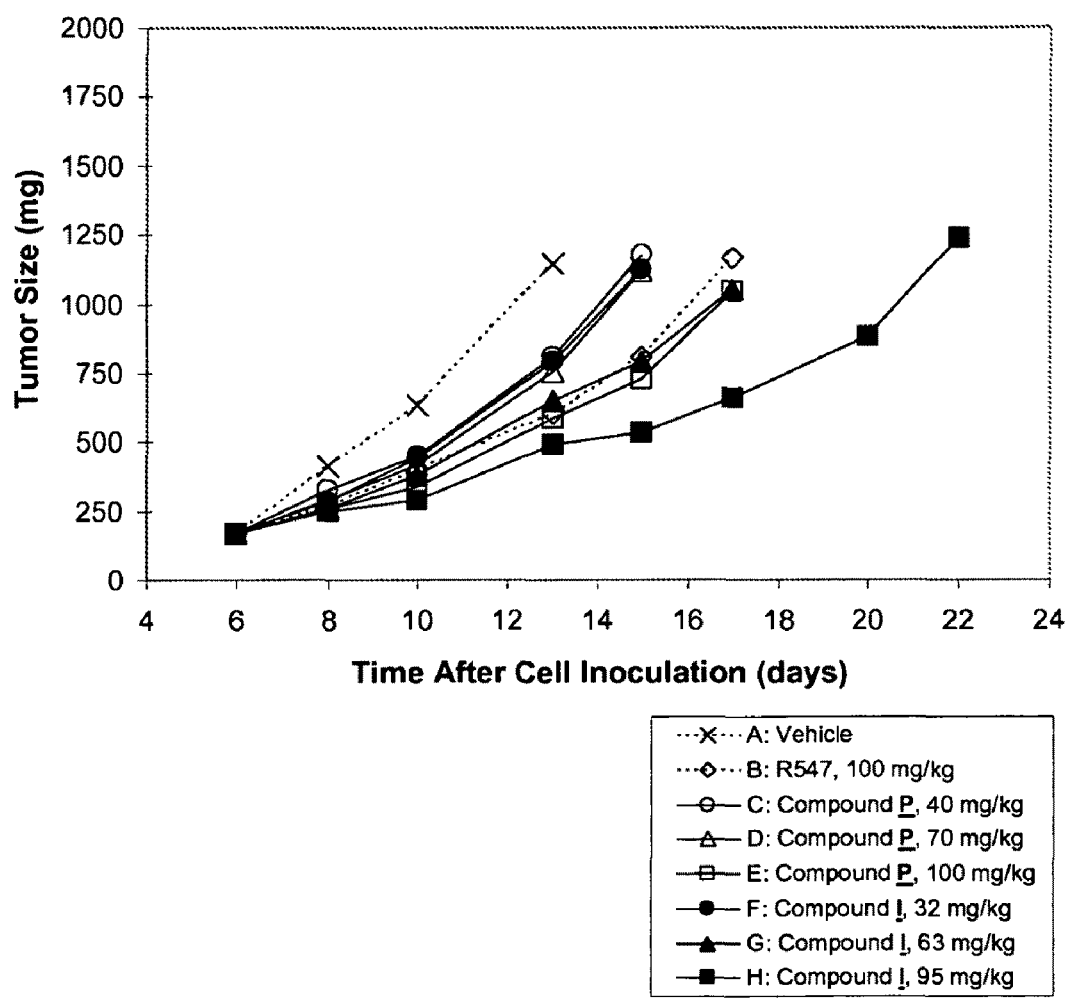
FIG. 4: Effects of daily oral administration of Compound I or Compound P (and the controls Vehicle and R547) on: (a) H460 lung xenograft tumor growth; and (b) mice body weight. Mean values for each group of mice is plotted at each time-point.
Figure 4:
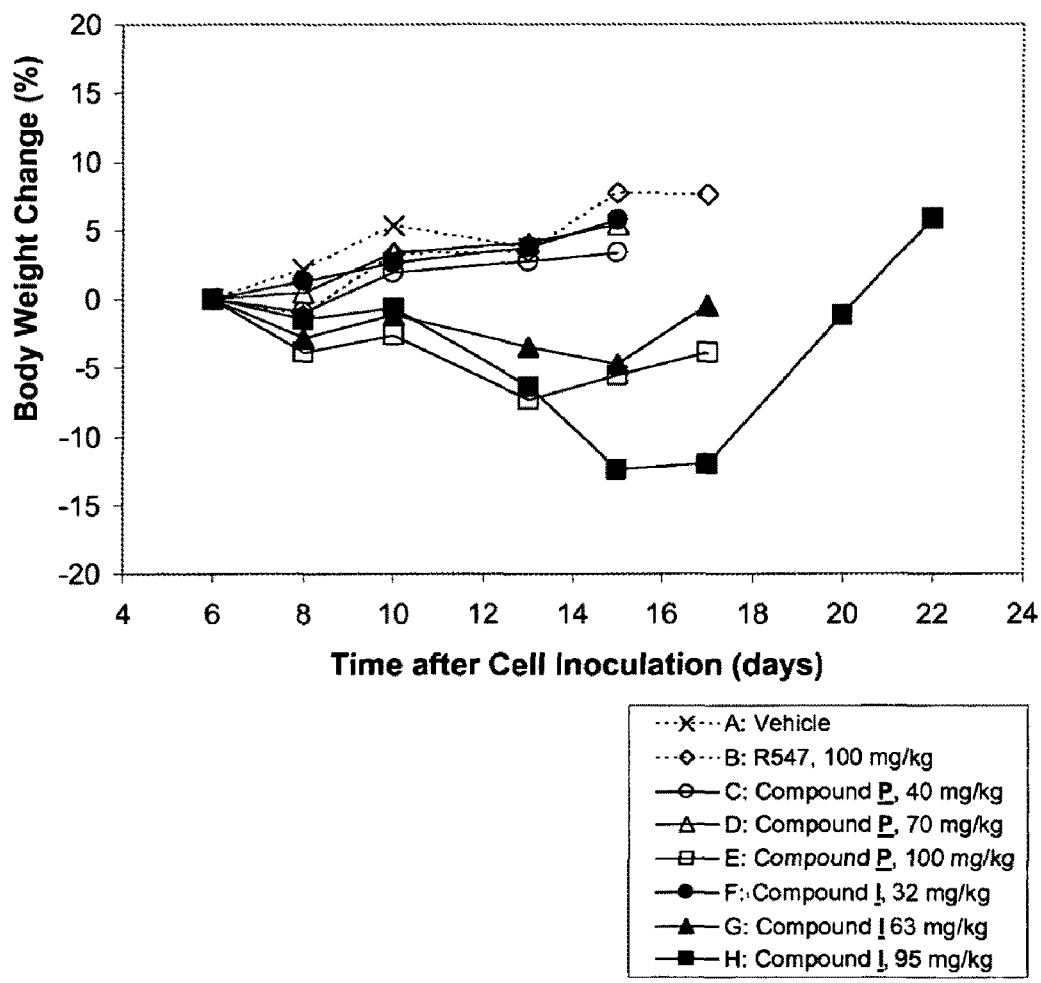

The in vivo doubling time of the H460 cells in this experiment was estimated as 2.6 days. Representative data are shown in FIG. 4, and summary results are tabulated below:

| Group | Treatment | Max % BW Loss (d) | Toxic Mortality | Max % TGI (d) | LCK ± CI (95%) ($T_d$: 2.6 d) |
|---|---|---|---|---|---|
| B | R547 | 1.3 (8) | 1/10 | 47.5 (13) | 0.48 ± 0.20 |
| C | P-40 mg | 1.0 (8) | 0 | 29.6 (13) | 0.22 ± 0.12 |
| D | P-70 mg | 0 | 0 | 33.9 (13) | 0.26 ± 0.12 |
| E | P-100 mg | 7.4 (13) | 0 | 48.7 (13) | 0.54 ± 0.17 |
| F | I-32 mg | 0 | 0 | 30.7 (13) | 0.26 ± 0.15 |
| G | I-63 mg | 4.7 (15) | 0 | 43.1 (13) | 0.48 ± 0.15 |
| H | I-95 mg | 12.5 (15) | 2/10 | 57.1 (13) | 0.97 ± 0.25 |

The surprising increase in anti-tumor activity of Compound I is shown by a LCK for a treatment group that is in each case larger than that for the group treated with a corresponding dose of Compound P. Indeed, pair-wise analysis of certain groups of mice by permutation test (see below), showed that Compound I showed a highly significant increased activity over Compound P (except for the lowest dosage for which no significant difference was observed; although even at this low dosage Compound I was significantly active compared to the control group A). Even more surprising was that at the highest dose (group H), Compound I was significantly more active than the positive control (group B), and that the highest dose of Compound P (group E) had only an equivalent LCK to that of the medium dose of Compound I (group G).

| Groups | Comparison | LCK estimates | Permutation Test p-Value | p < 0.10 |
|---|---|---|---|---|
| C-F | P-40 vs I-32 | 0.22 vs 0.26 | 0.7 | — |
| D-G | P-70 vs I-63 | 0.26 vs 0.48 | 0 | reject |
| E-H | P-100 vs I-95 | 0.48 vs 0.97 | 0 | reject |
| A-F | Vehicle vs I-32 | 0.00 vs 0.26 | 0 | reject |
| B-H | R547 vs I-95 | 0.48 vs 0.97 | 0 | reject |
| E-G | P-100 vs I-63 | 0.54 vs 0.48 | 0.4 | — |

Example C.4

Colon Cancer Model (HCT116 Cell-Line)

Daily Oral Administration

A comparative trial was designed having the protocol summarized in the following table, with the free-base equivalent dose indicated in square brackets. Compound P and Compound I were formulated as above, and were administrated p.o. every day for 10 days (qd×10). Mice in Group B were administered R547 (formulated as a suspension in 6% Cremophor EL®/40% PEG300/54% Saline) p.o. every day for 10 days.

| Group | Treatment | N | Dose (mg/kg, po) | Schedule |
|---|---|---|---|---|
| A | Vehicle (6% Cremophor EL ®/40% PEG300/54% Saline) | 10 | — | qdx10 |
| B | R547 | 10 | 100 | qdx10 |
| C | Compound P | 10 | 40 [37] | qdx10 |
| D | Compound P | 10 | 70 [65] | qdx10 |
| E | Compound P | 10 | 100 [93] | qdx10 |
| F | Compound I | 10 | 31.6 [29.5] | qdx10 |
| G | Compound I | 10 | 63.3 [59.1] | qdx10 |
| H | Compound I | 10 | 95 [89] | qdx10 |

Figure 5:
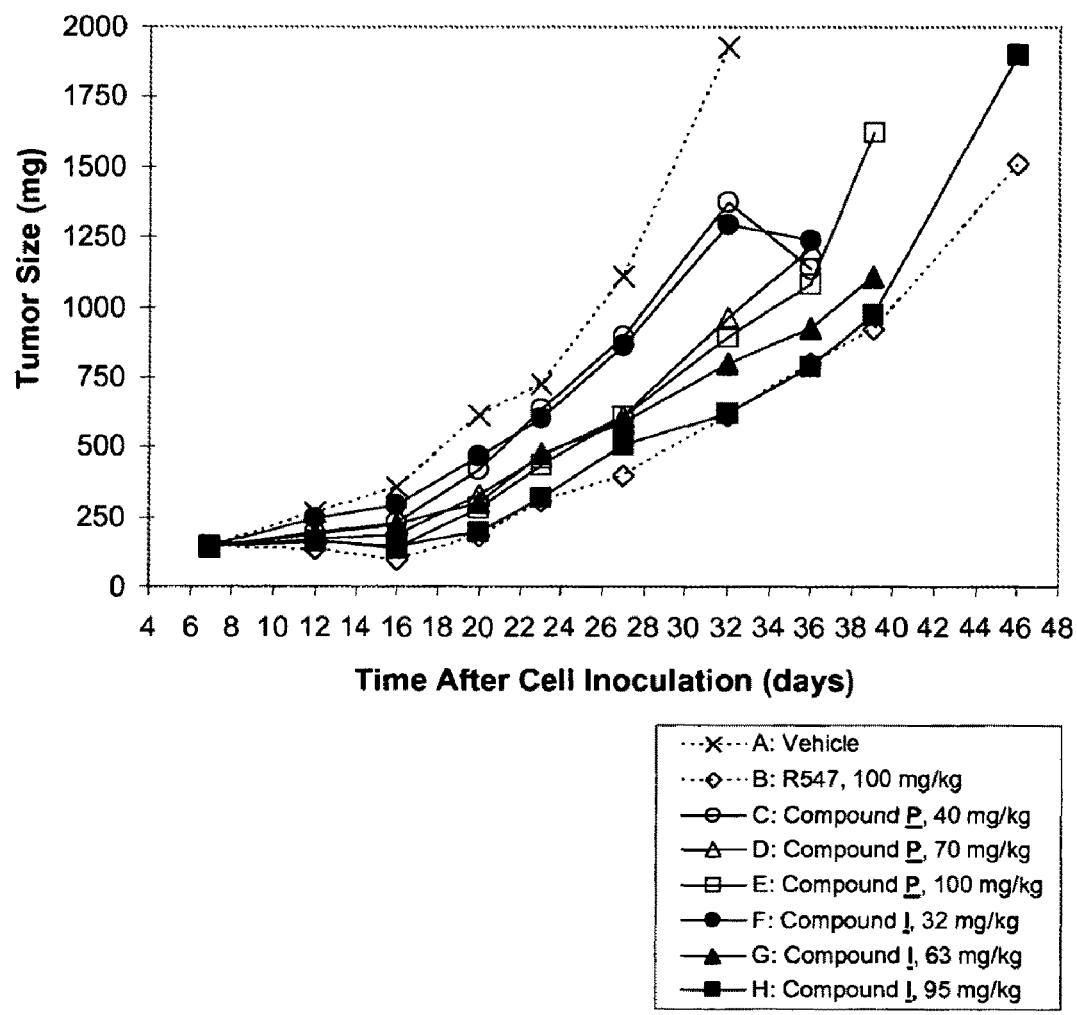
FIG. 5: Effects of daily oral administration of Compound I or Compound P (and the controls Vehicle and R547) on: (a) HCT116 colon xenograft tumor growth; and (b) mice body weight. Mean values for each group of mice is plotted at each time-point.
Figure 5:
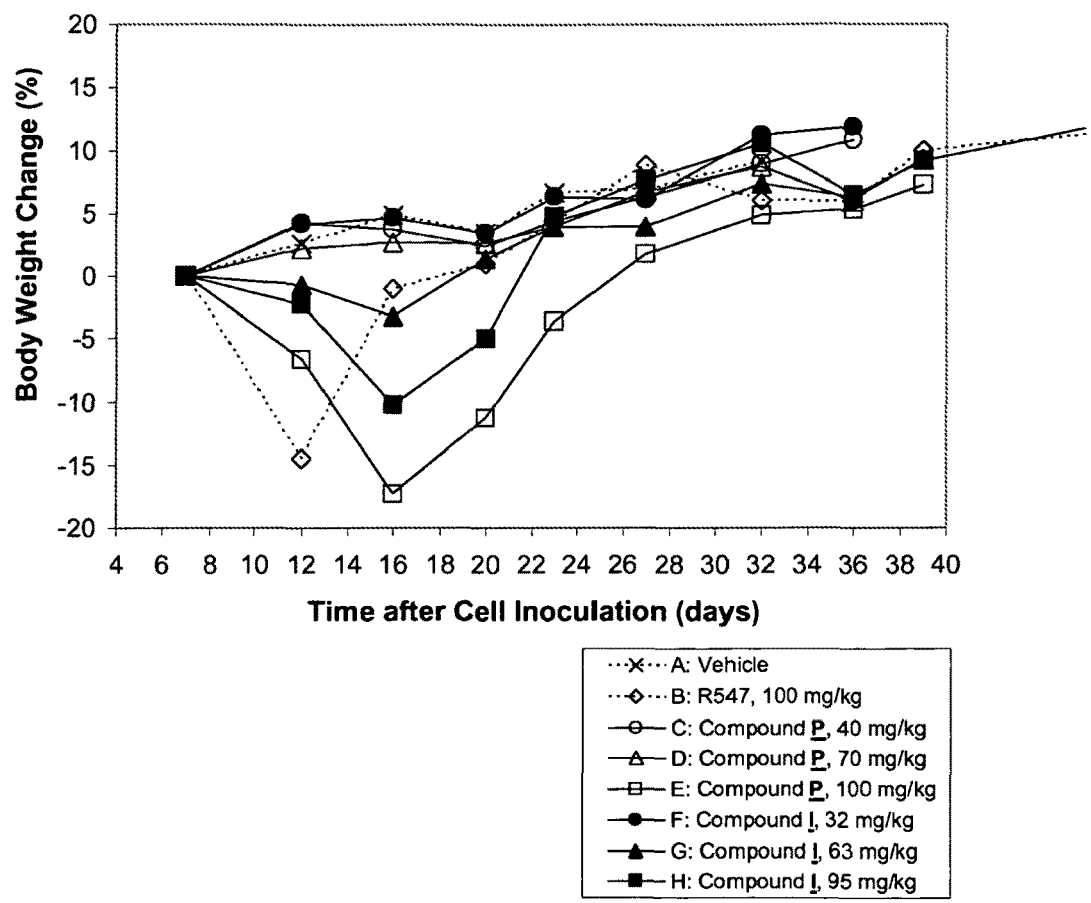

The in vivo doubling time of the HCT116 cells in this experiment was estimated as 6.8 days. Representative data are shown in FIG. 5, and summary results are tabulated below:

| Group | Treatment | Max % BW Loss (d) | Toxic Mortality | Max % TGI (d) | LCK ± CI (95%) ($T_d$: 6.8 d) |
|---|---|---|---|---|---|
| B | R547 | 14.5 (12) | 3/10 | 72.8 (16) | 0.70 ± 0.28 |
| C | P-40 mg | | | 36.2 (20) | 0.23 ± 0.11 |
| D | P-70 mg | | | 50.2 (32) | 0.41 ± 0.22 |
| E | P-100 mg | 17.3 (16) | 1/10 | 60.1 (16) | 0.38 ± 0.13 |
| F | I-32 mg | | | 32.7 (32) | 0.21 ± 0.08 |
| G | I-63 mg | 3.2 (16) | | 58.5 (32) | 0.51 ± 0.17 |
| H | I-95 mg | 10.2 (16) | 1/10 | 68.4 (20) | 0.60 ± 0.17 |

Compound I shows a general increase in anti-tumor activity, as estimated by LCK, for each dose (other than the lowest dose) as compared to the corresponding dose of Compound P. Pair-wise analysis of certain groups of mice by permutation test (see below) showed that Compound I showed a significantly increased activity over Compound P at the highest dosage, while the general superiority of Compound I over Compound P could not be significantly concluded using this stringent test, which was not able to reject the null-hypothesis at this level of significance for the two lower dosages.

| Groups | Comparison | LCK estimates | Permutation Test p-Value | p < 0.10 |
|---|---|---|---|---|
| C-F | P-40 vs I-32 | 0.23 vs 0.21 | 0.721 | — |
| D-G | P-70 vs I-63 | 0.41 vs 0.51 | 0.381 | — |
| E-H | P-100 vs I-95 | 0.38 vs 0.60 | 0 | reject |

Example C.5

Activity of the Subject Compound in In-Vivo Models of Other Human Cancers

The subject compound (Compound I) shows surprising and unexpected activity in other models of human cancers. This surprising activity is shown following i.v. or p.o. administration of the compounds in controlled murine xenograft experiments that can be conducted as described above. Tumor types for testing include: PC3 (prostate) and A2780 (lung). Experiments are conducted as described above, except that the appropriate tumor cell-line is used, and study compounds can, in certain experiments, be administered intravenously (i.v.) and as formulated appropriately.

Example D

Potent Inhibition of In-Cell RNAPII Phosphorylation by the Subject Compound

We were surprised to discover a novel mechanism of action for the anti-proliferative activity of subject compound in a number of human tumor cell lines. Unlike what is know in the art for 1-phenyl-pyrazolo[3,4-d]pyrimidin-4-ones (see, WO 00/021926; WO 03/033499; WO 2004/092139; WO 2005/063765; WO 2004/092139; WO 2005/063765; Caligiuri et al., *Chem Biol.* 12: 1103-15, 2005; Rossi et al., *Comput. Aided Mol. Des.* 19: 111-22, 2005; Markwalder et al., *J. Med. Chem.* 47: 5894-911, 2004), the subject compound I demonstrated an previously unknown mechanism of cellular activity as follows: compound I showed a pronounced and consistently potent ability to inhibit the cellular phosphorylation of RNAPII (driven by CDK9 activity) across a panel of mammalian tumor cell-models, while in contrast the cellular phosphorylation of Eg-5 and Rb (driven by CDK1 and CDK4/6 activity respectively) was both less strongly—and also far more variably—inhibited. Indeed, the cellular inhibition of CDK9-dependent RNAPII phosphorylation was better correlated to inhibition of antiproliferative activity by compound I, than to cellular inhibition of CDK1, or CDK4/6-dependent substrate phosphorylation.

Methodology:

CDK-dependent phosphorylation of the following substrates was investigated in cancer cells following treatment with compound I and R547 (DePinto et al., *Mol Cancer Ther.* 5: 2644-2658; 2006): (i) CDK1-dependent Eg-5 phosphorylation on threonine 927 (Blangy et al., 1995, Cell, 83(7): 1159-1169); (ii) CDK4/6-specific phosphorylation of Rb on serine 780 (Zarkowska & Mittnacht, J Biol Chem. 272(19): 12738-12746 1997; Connell-Crowley et al., Mol Biol Cell. 8(2): 287-301 1997; Kitagawa et al., 1996, EMBO J. 15(24): 7060-7069; Schmitz et al., 2006, Am J Pathol. 169(3): 1074-1079; Baughn, 2006, Cancer Res. 66: 7661-7667); (iii) CDK9-specific phosphorylation of RNA polymerase II (RNAPII) on serine 2 (Kim et al., 1997, J Cell Biol. 136(1): 19-28). This set of assays represents CDKs involved in cell cycle progression (CDK1, 4/6), and the "regulatory CDK" (CDK9) which is involved in transcriptional regulation.

Figure 6:
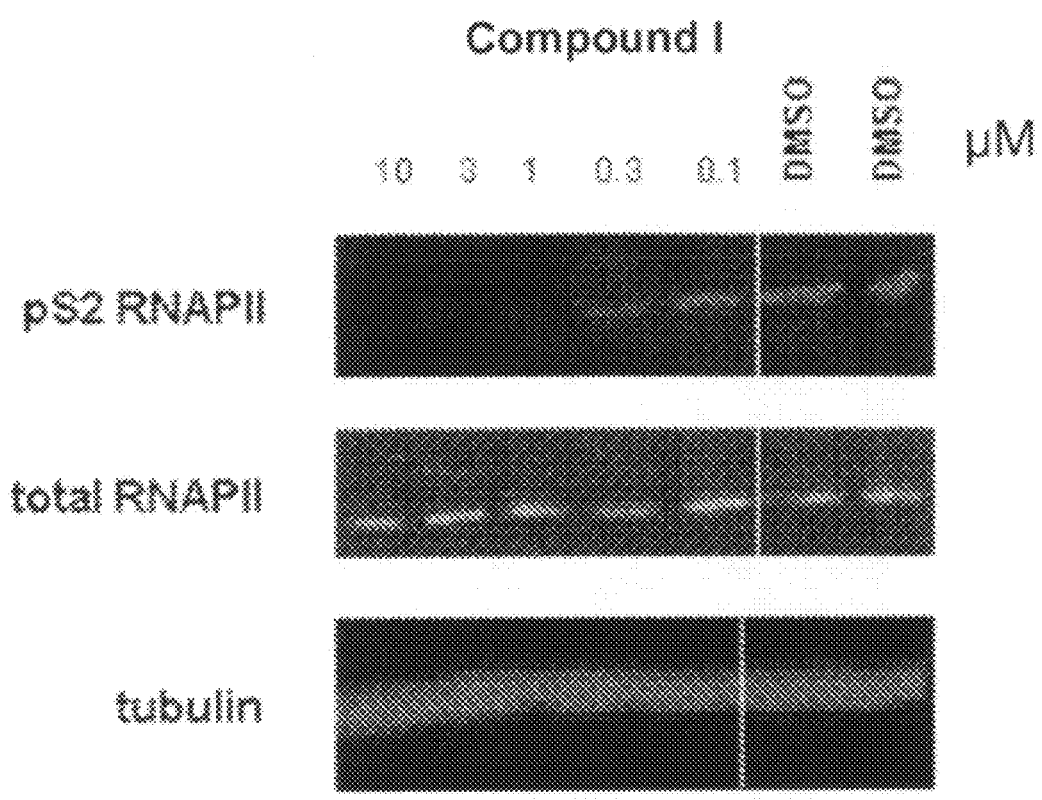
FIG. 6: Inhibition of CDK9-dependent RNAPII phosphorylation in HCT116 cells by compound I. Also shown are total RNAPII and tubulin protein as controls. Cells and lysates were processed as described in Example D.

The following cancer cell lines were investigated in the course of these studies: A2780 (ovarian), HCT116 (colon), RPMI8226 (myeloma), SKMel28 (melanoma), Colo205 (colorectal), MDA-MB-435 (melanoma), MDA-MB-453 (breast, carcinoma), MDA-MB-468 (breast, adenocarcinoma), A549 (lung), Raji (lymphoma, Burkitt). Cell lines were obtained from public repositories. Cells were treated at various concentrations of compound I or R547 for 1 h (Eg-5 and Rb phosphorylation) or 3 h (RNA polymerase II phosphorylation), the degree of substrate phosphorylation measured by immunoblot analysis and $IC_{50}$ values determined following quantification of the signals as described below. FIG. 6 shows an example of dose-dependent level of RNAPII phosphorylation in HCT116 cells on treatment with compound I as detected using the method described.

CDK9-specific phosphorylation of RNA polymerase II (RNAPII) on Serine 2 (Ser2). Asynchronous cells were treated with an appropriate concentration of test compound or DMSO as a control. After 3 h incubation (37° C./5% $CO_2$) cells were lysed with CLB-1 lysis buffer (Zeptosense, Switzerland), the lysate was cleared by centrifugation (10 min, 13000 rpm, RT) and subjected to SDS-PAGE. Total protein was blotted on PVDF membranes and analyzed using antibodies against S2-phosphorylated RNAPII (H5; Covance) or total RNAPII (N-20; Santa Cruz) as an expression control. Visualization was conducted using secondary Alexa680- or IR800-coupled antibodies (Molecular Probes) against mouse or rabbit Fc tails on the Odyssey-system (Licor). Specific bands were quantified and $IC_{50}$ values of inhibition of RNAPII phosphorylation were estimated.

CDK1-dependent Eg-5 phosphorylation on threonine 927 (Thr927phos). Thr927phos was investigated by arresting cells over night in G2/M phase with 25 ng/ml nocodazole (optimized final concentration) followed by treatment with DMSO as control or an appropriate concentration of test compound for 1 hour. Detached as well as adherent cells were collected and lysed with CLB-1 lysis buffer. the lysate cleared by centrifugation and subjected to SDS-PAGE. The proteins were blotted on PVDF membranes and subsequently analyzed by antibodies against total Eg-5 (Becton Dickinson) and Eg-5 Thr927phos (Bio legend). Visualization and estimation of $IC_{50}$ was conducted as above.

CDK4/6-specific phosphorylation of Rb on serine 780 (Ser780phos). Asynchronous growing cells were treated with an appropriate concentration of test compound or DMSO for 1 hour. Proteins were extracted using the AllPrep RNA/Protein kit according to the manufacturer's recommendations (Qiagen, Germany). Rb was immunoprecipitated over night using Ab05 antibody (Oncogene Inc.). Proteins were separated by SDS-PAGE, blotted to PVDF membranes and analyzed with antibodies against total (sc-102; Santa Cruz) or Ser780-phosphorylated Rb proteins (Cell Signalling). Visualization and quantification was performed as above.

Results:

The following tables show $IC_{50}$ values for inhibition of substrate-phosphorylation for CDK1, CDK4/6 and CDK9 by compound I or R547.

Compound I was a consistently potent inhibitor of CDK9-dependent phosphorylation of RNAPII, compared to the far less potent inhibition of such phosphorylation by R547. This distinction can be compared to the enzymatic $IC_{50}$s of CDK9 activity as estimated in biochemical assays as described earlier, are between about 1 to 10 nM for both compound I and R547.

| Cell line | Compound I $IC_{50}$ (uM) - RNAPII phosphorylation | R547 $IC_{50}$ (uM)) - RNAPII phosphorylation |
|---|---|---|
| A2780 | ~0.1 | ~1 |
| HCT116 | ~0.1 | ~0.3 |
| RPMI8226 | ~0.1 | ~0.5 |
| Sk-mel-28 | ~0.1 | ~0.3 |
| Colo205 | ~0.1 | ~0.5 |
| MDA-MB-468 | ~0.1 | ~0.3 |

In contrast, compound I shows a higher degree of variability in its potency of CDK1-dependent phosphorylation of Eg-5, compared to the relatively consistent IC50s in the same assays with R547. This consistency shows that the assays are reliable per se. In biochemical assays, R547 is a more potent CDK1 inhibitor than compound I ($IC_{50}$s for CDK1 are between about 1 and 10 nM and between about 10 and 50 nM, respectively).

| Cell line | Compound I $IC_{50}$ (uM) - Eg-5 phosphorylation | R547 $IC_{50}$ (uM)) - Eg-5 phosphorylation |
|---|---|---|
| A2780 | ~1 | ~0.01 |
| HCT116 | ~3 | ~0.1 |
| RPMI8226 | >1 | ~0.05 |
| Colo205 | ~1 | ~0.05 |
| MDA-MB-435 | ~0.5 | ~0.1 |
| MDA-MB-453 | ~1 | ~0.1 |
| A549 | >1 | ~0.03 |
| Raji | >1 | ~0.1 |

Variability in potency compared to R547 is also seen in potency of inhibition of CDK4/6-dependent phosphorylation of Rb. R547 is a moderately more potent CDK4 and CDK6 inhibitor ($IC_{50}$s for CDK4 and CDK6 in both cases about 10 nM) than compound I ($IC_{50}$s for CDK4 and CDK6 about 50 nM, and between about 10 and 50 nM, respectively).

| Cell line | Compound I $IC_{50}$ (uM) - Rb-5 phosphorylation | R547 $IC_{50}$ (uM)) - Rb-5 phosphorylation |
|---|---|---|
| A2780 | ~0.5 | ~0.1 |
| HCT116 | ~5 | ~0.1 |
| RPMI8226 | ~5 | ~0.3 |
| Sk-mel-28 | ~3 | ~0.1 |
| Colo205 | ~1 | ~0.1 |
| MDA-MB-435 | ~3 | ~0.3 |

When compared to $IC_{50}$s of cellular proliferation by compound I, (as determined by the methods described earlier), the corresponding $IC_{50}$ for cellular inhibition of CDK9-dependent RNAPII phosphorylation is approximately similar. This is in contrast to the far more variable and in many cases less potent $IC_{50}$ for CDK1 or CDK4/6 substrate phosphorylation.

| $IC_{50}$ (uM) Compound I | Cell proliferation | CDK1 Eg-5 phosphorylation | CDK4/6 Rb phosphorylation | CDK9 RNAPII phosphorylation |
|---|---|---|---|---|
| A2780 | ~0.1 | ~1 | ~0.5 | ~0.1 |
| HCT116 | ~0.1 | ~3 | ~5 | ~0.1 |
| Sk-mel-28 | ~0.3 | n.d. | ~3 | ~0.1 |
| Colo205 | ~0.1 | ~1 | ~0.1 | ~0.1 |
| MDA-MB-468 | ~0.3 | n.d. | n.d. | ~0.1 |

Without being bound by theory, these data suggest the surprising hypothesis that the cytotoxic activity of compound I in mammalian cell models of human cancer is mediated through at least the inhibition of CDK9 activity, and in certain situations with reduced concomitant inhibition of CDK1, CDK4 or CDK6 activity.

Example E

Selection and Development of Pharmaceutical Compositions

In order to (i) select the most appropriate active ingredient form, i.e. compound I as such, a pharmaceutically acceptable salt of compound I, or a prodrug of compound I, to enter further experiments and to assess its suitability for use in a therapeutic composition for the treatment of disorders and diseases, such as cancers; (ii) select the most appropriate pharmaceutical composition including the active ingredient so identified, and (iii) select the most appropriate indication for using such pharmaceutical composition, additional data are collected. Such data can include the in vitro inhibition of proliferation across a panel of tumor cell lines, and tumor growth inhibition or reduction data and survival data from in vivo animal models. Furthermore, such experiments may also include the elucidation and/or determination of the mechanism of action of the subject compound, the target or target profile of the subject compound, and other characteristics of the subject compound, such as the binding affinity of the compound to the target(s) or the binding site of the compound on the target(s) and pharmacokinetic properties. Such experiments may also include molecular modeling of the drug-target interaction and the identification of metabolites formed after administration, or identification of the active agent.

The active ingredient and/or pharmaceutical composition including such active ingredient that shows the most appropriate results, including results for inhibition of cell proliferation, spectrum across various tumor cell lines, inhibition of tumor growth or tumor reduction data and/or animal-survival data, and/or other features, including ADMET, pharmacokinetic and pharmacodynamic properties, may be chosen to enter further experiments. Such experiments may include, for example, therapeutic profiling and toxicology in animals, phase I clinical trials in humans and other clinical trails.

One skilled in the art readily appreciates that the present invention is well adapted to carry out the objects and obtain the ends and advantages mentioned, as well as those inherent therein. The methods and reagents described herein are representative of preferred embodiments, are exemplary, and are not intended as limitations on the scope of the invention. Modifications therein and other uses will occur to those skilled in the art. All such obvious modifications and alternative uses are encompassed within the spirit of the invention and are intended to be included within the scope of the appended claims.

All of the above-cited references and publications are hereby incorporated by reference.

I claim:
1. A compound having the structure of formula (I),

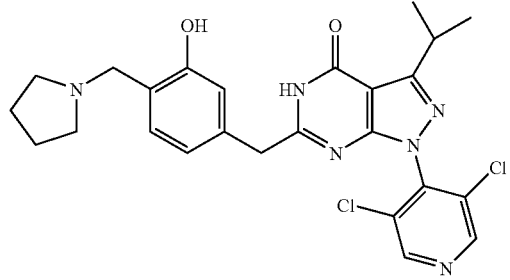

or a tautomer, or pharmaceutically-acceptable salt thereof.

2. The compound according to claim 1 wherein said pharmaceutically-acceptable salt is a hydrochloride salt or a maleate salt.

3. A pharmaceutical composition comprising an active ingredient comprising a compound of claim 1, or a pharmaceutically acceptable salt thereof, and a pharmaceutically acceptable diluent, excipient or carrier.

4. The pharmaceutical composition of claim 3 wherein said composition is formulated for oral administration.

5. The pharmaceutical composition of claim 3 wherein said composition is formulated for intravenous administration.

6. The pharmaceutical composition of claim 3, comprising a therapeutically effective amount of said active ingredient.

7. A method of synthesizing a compound of claim 1 or optionally a salt thereof, comprising reacting a compound having the structure of formula (II) with a compound having the structure of formula (III),

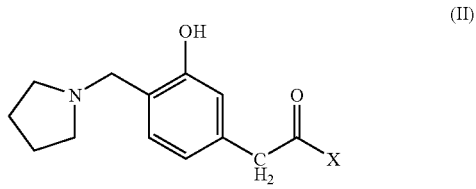

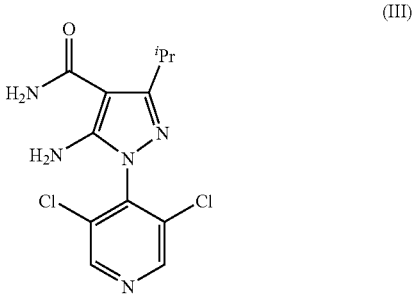

wherein X is selected from —O-alkyl, —O-alkenyl, —O-alkynyl, —O-acyl, and halogen; and, optionally, reacting the resultant compound with an acid to make an acid salt.

8. The method of claim 7, wherein X is —OEt.

9. A method of synthesizing the pharmaceutically acceptable salt of claim 1, comprising reacting the compound of claim 1 with an acid.

10. The method of claim 9, wherein the acid is hydrochloric acid or maleic acid.

* * * * *